United States Patent
Tajima

(10) Patent No.: US 8,921,282 B2
(45) Date of Patent: *Dec. 30, 2014

(54) SEGMENTED PROCESS APPARATUS FOR MICROPLATE AND SEGMENTED PROCESS METHOD FOR MICROPLATE

(75) Inventor: Hideji Tajima, Matsudo (JP)

(73) Assignee: Universal Bio Research Co., Ltd., Matsudo-Shi, Chiba (JP)

( * ) Notice: Subject to any disclaimer, the term of this patent is extended or adjusted under 35 U.S.C. 154(b) by 1492 days.

This patent is subject to a terminal disclaimer.

(21) Appl. No.: 12/310,616
(22) PCT Filed: Aug. 30, 2007
(86) PCT No.: PCT/JP2007/066840
§ 371 (c)(1), (2), (4) Date: Jul. 29, 2010
(87) PCT Pub. No.: WO2008/026670
PCT Pub. Date: Mar. 6, 2008

(65) Prior Publication Data
US 2010/0285996 A1 Nov. 11, 2010

(30) Foreign Application Priority Data
Aug. 30, 2006 (JP) .................................. 2006-234444

(51) Int. Cl.
C40B 60/14 (2006.01)
C12M 1/00 (2006.01)
B01L 3/00 (2006.01)
G01N 21/00 (2006.01)
G01N 35/10 (2006.01)
G01N 35/02 (2006.01)

(52) U.S. Cl.
CPC .......... *G01N 35/1074* (2013.01); *G01N 35/028* (2013.01)
USPC .......... 506/27; 435/283.1; 422/501; 422/521; 422/82.05

(58) Field of Classification Search
None
See application file for complete search history.

(56) References Cited

U.S. PATENT DOCUMENTS 5,702,950 A 12/1997 Tajima
6,509,193 B1 1/2003 Tajima
(Continued)

FOREIGN PATENT DOCUMENTS

JP 08-062224 3/1996
JP 2000-023657 1/2000
(Continued)

OTHER PUBLICATIONS

International Search Report issued Oct. 9, 2007, by the ISA/JP, in connection with International Application No. PCT/JP2007/066840.

(Continued)

*Primary Examiner* — Betty Forman
(74) *Attorney, Agent, or Firm* — Haynes and Boone, LLP

(57) ABSTRACT

An object is to provide a highly effective segmented process apparatus for a microplate using a standard microplate without increasing the scale of the apparatus, as well as a method for processing a microplate. The apparatus includes: a predetermined microplate provided with a number of wells are set in array; one or more nozzle heads provided with a number of nozzles set in array; a suction and ejection mechanism for sucking and ejecting a gas via the nozzles; and a moving means which allows relative movement between the microplate and the nozzle heads, wherein tips of all of the nozzles provided on each nozzle head are provided in such a manner that the tips can be inserted into the wells in a portion of the microplate all together, and the row intervals and column intervals of the nozzles in array are respectively same as the row intervals and column intervals of the wells in array.

9 Claims, 14 Drawing Sheets

(56) References Cited

U.S. PATENT DOCUMENTS

| | | |
|---|---|---|
| 6,691,748 B1 * | 2/2004 | Tajima .................. 141/130 |
| 6,805,840 B1 | 10/2004 | Tajima |
| 7,105,357 B1 * | 9/2006 | Kalkum et al. ............ 436/180 |
| 2003/0012699 A1 * | 1/2003 | Moore et al. .............. 422/100 |
| 2003/0026732 A1 * | 2/2003 | Gordon et al. ............. 422/63 |
| 2006/0121612 A1 * | 6/2006 | Tajima et al. ............. 435/459 |
| 2008/0096285 A1 | 4/2008 | Koyata et al. |
| 2010/0043575 A1 * | 2/2010 | Tajima ................. 73/864.11 |
| 2010/0047132 A1 * | 2/2010 | Tajima .................. 422/101 |

FOREIGN PATENT DOCUMENTS

| | | | |
|---|---|---|---|
| JP | 2001-108694 | | 3/2005 |
| WO | WO 97/044671 | | 11/1997 |
| WO | WO 99/47267 | | 9/1999 |
| WO | WO9961881 | * | 12/1999 |
| WO | WO 2006/011531 | | 2/2006 |

OTHER PUBLICATIONS

Written Opinion issued Oct. 9, 2007, by the ISA/JP, in connection with International Application No. PCT/JP2007/066840.

International Preliminary Report on Patentability issued Aug. 12, 2008, by the IPEA/JP, in connection with International Application No. PCT/JP2007/066840.

* cited by examiner

US 8,921,282 B2

SEGMENTED PROCESS APPARATUS FOR MICROPLATE AND SEGMENTED PROCESS METHOD FOR MICROPLATE

CROSS REFERENCE

This application is a United States national phase application of co-pending international patent application number PCT/JP2007/066840, filed Aug. 30, 2007, which claims priority to Japanese patent application number 2006-234444, filed Aug. 30, 2006, the disclosures of which are incorporated herein by reference.

TECHNICAL FIELD

The present invention relates to a segmented process apparatus for a microplate and a segmented process method for a microplate.

BACKGROUND ART

Microplates are provided with a number of wells arranged in a matrix form (in array) which can contain a liquid, and 12 rows×8 columns (96 wells, row intervals and column intervals of 9 mm), 24 rows×16 columns (384 wells, row intervals and column intervals of 4.5 mm), 48 rows×32 columns (1536 wells, row intervals and column intervals of 2.25 mm) and the like are known, and tend to be standard internationally. Here, row intervals are the distance between the center of a well or the center line of the row in which the well is provided and the center of a neighboring well in the column direction or the center of the row along which the well is provided in the column direction, and the column intervals are the distance between the center of a well or the center line of the column in which the well is provided and the center of a neighboring well in the row direction or the center line of the column in which the well is provided in the row direction.

In the case where a simultaneous process is carried out using a number of types of liquids together using such a microplate, a dispenser apparatus having one nozzle head on which nozzles or nozzles for attachment of which the number is equal to the total number of wells in the microplate on which a dispenser tip is mounted is used, and all of the nozzles are inserted into the wells together for each microplate, where the same type or same amount of solutions or suspension liquids is sucked up and ejected, is used (Patent Document 1).

In the case where a sequence of processes is carried out by making a number of types of reagents react with a great number of test substances sampled from a great number of specimens to be processed in sequence, for example, the same number of microplates having wells of which the number is in accordance with the number of the specimens, which of microplate is the same as the number of steps or types of necessary reagents in the process, is prepared in order to contain reagent solutions, specimens and magnetic particle suspension liquids which are necessary for the process. The apparatus, which can make the magnetic particles adsorbed in the inner walls of the dispenser tips corresponding to the nozzles, is used so that magnetic particles are moved to the wells of a number of microplates in sequence, and a process for inducing reaction through suspension within the wells is carried out in sequence (Patent Documents 1 and 2).

Thus, when a great number of types of reagents are used for the process, the number of microplates is great, because one microplate is allocated for each type, and thus, the area for work becomes large. In addition, the distance over which the nozzle heads move corresponds to the distance over which the nozzle heads move when passing through all of the microplates of which the number of types of reagents required for the process, and therefore, when the number of microplates is great, the distance over which the nozzle heads move becomes great, and thus, there is a problem, such that there is a risk that it may not be possible to carry out the process quickly and efficiently.

In addition, in the case where the number of specimens is not so great and microplates of which the number corresponds to the number of specimens and the number of process steps are prepared, it is necessary to use a nozzle head where nozzles are aligned with row intervals and column intervals corresponding to the row intervals and column intervals of the wells arranged in the microplate, and thus, it is necessary to prepare other nozzle heads in accordance with the number of specimens.

Meanwhile, in the case where microplates with which cases of a great number of specimens can be dealt with are used when the number of specimens is small, and in the case where the liquids used in the process steps are aligned in one column or one row, and a nozzle head having nozzles aligned in one corresponding column or row is used, the maximum number of specimens is limited to the number in one row or column, and thus, in the case where the number of specimens exceeds the number in one row or column, there is a problem, such that there is a risk that it may be difficult to handle.

In particular, in the case where the number of specimens exceeds the number of nozzles in one row or column but the number is a divisor of the total number of the wells, and the divisor is a multiple of two numbers, there is a possibility that one microplate may be segmented so that the process can be completed without waste.

When the number of processes carried out in parallel is great, the number of wells in the microplates is great, making integration more necessary, and in addition, it is necessary to provide nozzles so as to be closer together, and therefore, the intervals between dispenser tips are small and the area occupied by the dispenser tips is small, and thus, there is a problem, such that there is a risk that the built-in function of the dispenser tips deteriorates.

[Patent Document 1] International Unexamined Patent Publication WO99/47267
[Patent Document 2] Japanese Patent No. 3115501

DISCLOSURE OF THE INVENTION

Problem to Be Solved by the Invention

The present invention is provided in order to solve the above described problems, and a first object thereof is to provide a segmented process apparatus for a microplate which uses standard microplates and can handle a greater number of types of solutions or suspension liquids, or a greater volume of solutions or suspension liquids per area for work or volume of the apparatus without increasing the scale of the apparatus, as well as a method for processing a microplate. A second object is to provide a multipurpose segmented process apparatus for a microplate with which a process can be carried out irrespectively of the number of wells in the microplates even in the case where the number of objects to be processed together is smaller than the number of wells in the standard microplate, as well as a segmented process method for a microplate. A third object is to provide a segmented process apparatus for a microplate which is highly functional even when microplates where a great number of wells are integrated are handled, as well as a segmented process method for a microplate.

Means for Solving Problem

The first invention provides a segmented process apparatus for a microplate including: a predetermined microplate provided with a number of wells set in array; one or more nozzle heads provided with a number of nozzles set in array; a suction and ejection mechanism for sucking and ejecting a gas via the nozzles; and a moving means which allows relative movement between the microplate and the nozzle heads, wherein tips of all of the nozzles provided on each nozzle head are provided in such a manner that the tips can be inserted into the wells in a part of the microplate all together, and the row intervals and column intervals of the nozzles in array are respectively same as the row intervals and column intervals of the wells in array.

Here, "in array" means a configuration where elements, for example wells or nozzles, of a predetermined number in row direction and a predetermined number in column direction are arranged with predetermined row intervals and column intervals, and the number in row direction and the number in column direction are respectively two or more, and preferably three or more. Here, the columns and rows usually cross at a right angle, but the invention is not necessarily limited to this arrangement, and they may cross obliquely. In addition, adjacent rows or adjacent columns may be shifted by half the distance of the intervals between columns or half the intervals between rows, so that the elements are aligned in zigzag so as to be closest packed. "Row intervals" are the distance between the center of one element in the array or the center line of the row including the element and the center of the adjacent element in the column direction or the center line of the row including such element, while "column intervals" are the distance between the center of one element in the array or the center line of the column including the element and the center of the adjacent element in the row direction or the center line of the column including such element.

"Microplate" is a container provided with a predetermined number of wells set in array with predetermined row intervals and column intervals. Microplates where the row intervals and column intervals are set in accordance with the number (number of rows and number of columns) (for example the size and form of the entirety of the container are set constant in advance and the row intervals and the column intervals are set so that wells of the number are arranged at equal intervals within the container, that is to say, the row intervals and column intervals are functions of the number of the wells) are referred to as standard microplates. Standard microplates having row intervals and columns intervals that are same distance are referred to as regular microplates, and regular microplates where a predetermined, standard number of wells (number of rows and number of columns) are set in array at predetermined, standard regular row intervals (that is, same as the standard regular column intervals) defined in accordance with the number of wells are referred to as standard regular microplates. "Standard regular microplates" include worldwide standard microplates with 96 wells in 12 rows×8 columns, microplates with 384 wells in 24 rows×16 columns, and microplates with 1536 wells in 48 rows×32 columns, and their standard, and there standard regular row intervals (that is, same as the standard regular column intervals) are respectively 9 mm, 4.5 mm and 2.25 mm. The material for microplates is resin, such as polyethylene, polypropylene, polyester, polystyrene, polyvinyl or acryl.

"Part of microplate" may mean a part of wells belonging to the standard (or regular, or standard regular) microplates or, may mean a part of or all of wells belonging to sub standard (or regular, or standard regular) microplates having the wells of a smaller number than standard (or regular, or regular standard) number arranged in array at standard (or regular, or regular standard) row intervals and standard (or regular, or regular standard) column intervals, which are defined in accordance with the standard (or regular, or regular standard) number of wells.

"Nozzle" is a portion through which fluid is sucked or ejected, and fluid may be gas or liquid. The Nozzle has a cylinder having a plunger or a flow path connected to a mechanism for sucking or ejecting a fluid by due to a change of a bellow or an elastic body. In addition, nozzle may include a flow path, such as a dispenser tip attached to a nozzle for attachment. In addition, it is preferable to provide a pressure sensor on the nozzle for detecting change in pressure within the nozzle.

"The tips of all of the nozzles are provided in such a manner that they can be inserted into the wells in a part of the microplate all together", and therefore, the number of rows or number of columns of nozzles in array is smaller than that of wells in array, and the angle formed between the direction of rows and the direction of columns is the same between the nozzles in array and the wells in array. It is necessary for the row intervals or column intervals between columns of nozzles in array to be a natural number multiple of the intervals between rows or columns of wells in array, and "row intervals and column intervals of said nozzles in array are respectively same as the row intervals and column intervals of said wells in array", and thus, the natural number is one.

The second invention provides the segmented process apparatus for a microplate wherein the microplate includes a number of sub-arrays of wells into each of which the tips of all of the nozzles provided on the nozzle head can be inserted all together, and each of the sub-arrays does not include a well overlapping with each other.

The microplate contains a number of sub-arrays of wells into each of which the tips of all of the nozzles provided on the nozzle head can be inserted all together, and each of the sub-arrays does not include a well overlapping with each other, that is to say, the microplate includes at least two wells-in-matrix-forms of the same arrangement as that of nozzles in a matrix form, which do not include a well overlapping with each other.

As a result, it is possible to restrict the work area within one existing microplate even in the case where the number of samples to be processed, such as specimens, is small, and a number of process steps are required, and therefore, the work area does not become excessively large. In addition, the tip of all of the nozzles on the nozzle head can be located in such a manner that the tips can be inserted into the all sub-arrays of wells only within the microplate by repeatedly moving the nozzle head across sub-arrays of wells in the number of times same as the number of sub-arrays of wells within the microplate.

"The row intervals and column intervals of the nozzles in array are respectively same as the row intervals and column intervals of the wells in array", and therefore, at least a natural number (>1) of areas of sub-arrays which have the same arrangement as nozzles in array and which do not include a well overlapping with each other are included in the microplate, that is to say, the microplate is segmented into areas which correspond to an area where the nozzles in array are arranged in the nozzle heads with straight border lines.

As a result, the work area can be limited within one microplate, and therefore, the work area does not become excessively large. In addition, the movement of the nozzle head between the sub-arrays of wells can be limited within the microplate.

Here, the number of the nozzle heads and the number of microplates are the same as the number of the sub-arrays of wells in each of the microplates, and thus, comparing to the case where a nozzle head having all nozzles in array of a matrix form and number corresponding to all wells in array included in a microplate is used, in the case where the same number of specimens are processed using a nozzle head having the same number of nozzles, an efficiency will be the number of the nozzle heads times higher.

The third invention provides a segmented process apparatus for a microplate, further including a magnetic force means having a magnet provided in such a manner that the magnet is movable toward and away from said nozzles along a straight line or a curve that passes in the vicinity of each of the nozzles without crossing either of the nozzles, so that it is possible to apply a magnetic field to and remove a magnetic field from inside each of the nozzles provided on the nozzle head all together.

The straight line preferably runs in the row direction or column direction so as to be adjacent to the nozzle row or nozzle column, and the curve preferably shows a straight line when projected on the horizontal surface in the periphery of the nozzles and runs in the column direction or the row direction, such as an arc. Straight lines are lines which extend infinitely, however "something is movable toward and away along" a line segment as a part of the straight line. "Crossing of the nozzles and the straight line or a curve" includes cases where the straight line or a curve or an extended portion thereof crosses the nozzle or passes through the nozzle, hits against the nozzle or collides with the nozzle. "The vicinity of the nozzle" is the proximity over which the magnetic field can be applied effectively to inside a nozzle, including contacting with the nozzle. It is preferable for the number of straight lines or curves to be smaller than the total number of nozzles provided on the nozzle head. More preferably, the number is (number of rows+1) or (number of columns+1) of the nozzles or less.

"Movable toward or away from" means that it is possible to move toward and away from an object. "Movable toward" is, in other words, an object arrives at a location in the vicinity of the nozzle. In order for the magnetic force means to be "movable toward or away from" the nozzle head, the magnetic force means and the nozzle head may be provided in different places and then the magnetic force means may be moved toward or away from the nozzle using the moving means, the magnetic force means may be provided on the nozzle head and may be moved by using a moving toward/away means separate from the moving means, or the magnetic means may be moved toward or away from the nozzle using both of a part of the moving means and a means other than the moving means. As a result, in the case where the number of rows and the number of columns are three or more, respectively, that is to say, nozzles are set in array with 3 rows or more×3 columns or more, the nozzles can be integrated with such a density that intervals between nozzles can be set to allow for a space through which a magnet can pass without securing a distance over which a magnet recedes not to apply magnetic field as the intervals between nozzles. Here, the magnetic force means can generally be applied to apparatuses for processing microplates including: a microplate provided with wells set in array; one or more nozzle heads provided with a number of nozzles set in array; a suction and ejection mechanism for sucking and ejecting a gas via the nozzles; and a moving means which allows relative movement between the microplate and the nozzle head. The "object" is the nozzle or the axis line of the nozzle, and the axis line of the nozzle is a straight line extending along the axis of the nozzle. "Magnet" may be a permanent magnet and an electromagnet.

The fourth invention provides a segmented process apparatus for a microplate wherein the magnetic force means includes: one or more comb teeth members in rod form, which extend in the row direction or the column direction and which are correspondingly aligned in the column direction or the row direction so as to come adjacent to one or two nozzle rows or nozzle columns; a support member connected to one or more of the comb teeth members at one end and is movable relative to the nozzles; and magnets provided in each comb teeth member in locations corresponding to the nozzles belonging to the one or two nozzle rows or nozzle columns adjacent to each other. Here, at least one of the comb teeth members can be inserted between the rows of nozzles or between the columns of nozzles, and the direction in which the support member moves is the direction of columns or the direction of rows.

Here, the number of the comb teeth members is (row number−1) or (column number−1) of the nozzles in the case where a magnetic field from one magnet is applied only to adjacent nozzles, that is, in the case where the members are provided so that they can be inserted only between the rows of the nozzles or the columns of the nozzles, the same number of rows or columns, of the nozzles in the case where the members are provided outside the nozzle rows or nozzle columns, and the number of rows/2, (number of rows+1)/2, the number of columns/2 or (number of columns+1)/2 in the case where a magnetic field from one magnet is applied to two adjacent nozzles. In the case where more than one magnetic field is not applied to one nozzle, two or more comb teeth members are provided when the number of rows and columns is three or more. The path of movement of the magnets provided in the comb teeth members relative to the nozzles runs along a straight line or a curve, which does not cross the nozzles.

The fifth invention provides a segmented process apparatus for a microplate further including a control portion, wherein the control portion controls the moving means to perform an operation, in which the moving means relatively moves between the nozzle head and the microplate so that the tips of all of the nozzles provided on the nozzle head are in such locations where the tips can be inserted into the wells belonging to one of the sub-arrays of the wells in the microplate, and then moves to insert the tips of the nozzles into the wells all together and to remove the tips after a certain process, and the operation is repeated in sequence for the wells belonging to other sub-arrays of wells.

In particular, in the case where the number of specimens does not coincide with the number of rows or the number of columns in the microplates, and the number of specimens is a divisor of the number of wells in the microplate with the number of specimens not a prime number, the arrangement of the nozzles is in the form of a matrix when processed, and thus, the microplate can be efficiently used. In the case where the number of specimens is 16 with a microplate having 96 wells in 12 rows×8 columns, for example, the number of nozzles is different from the number of rows, number of columns or total number of wells, and 16 is a divisor of 96, but not a prime number, and therefore, a nozzle head where nozzles in 4 rows×4 columns are aligned is used, and at the same time, the microplate is segmented into six sub-arrays of 4 rows×4 columns, and thus, the microplate can be used without waste, using the nozzle head.

The sixth invention provides a segmented process apparatus for a microplate wherein solutions or suspension liquids required for the steps in the process are contained in each of the number of sub-arrays of wells along the moving path of the nozzle head in accordance with the order of the steps.

Here, the "moving path" is a path through which the nozzle head passes when it is translated over all of the sub-arrays in sequence, and the shortest path in terms of the distance along the moving path is preferable. Accordingly, sub-arrays of wells are selected in sequence in the order following the process steps, and necessary solutions, such as reagents, are contained accordingly. In addition, the same kind and the same amount of solution or suspension liquid to be handled is contained in wells belonging to the same sub-array of wells, for example, and different kinds or different amounts of solution or suspension liquid to be handled are contained in wells belonging to different sub-arrays of wells. This is because the operations for suction and ejection through the nozzles provided on the same nozzle head link to each other, and thus are substantially the same. Alternatively, in the case where a large volume of liquid is handled, the same type of solution or suspension liquid is sometimes contained in wells belonging to different sub-arrays of wells.

The seventh invention provides a segmented process apparatus for a microplate wherein each of the nozzles provided on the nozzle head has a nozzle for attachment and a dispenser tip detachably attached to the nozzle for attachment, and the nozzle head has a tip detaching portion for detaching a dispenser tip attached to the nozzle for attachment.

The eighth invention provides a segmented process apparatus for a microplate further including a light detecting means having a light detecting portion provided in such a manner that the light detecting unit is movable toward each of the nozzles in sequence along a straight line or a curve that passes in the vicinity of each of the nozzles without crossing either of the nozzles so that it is possible to detect the state of the liquid inside the nozzles provided on the nozzle head in sequence. Accordingly, it is necessary for the dispenser tip mounted on the nozzles or the nozzles for attachment to be formed of a light transmitting member. The object to be detected is the state of the liquid, for example, and the state includes the existence of a liquid, the level of the liquid, the surface of the liquid, the amount of sucked up liquid and the amount of ejected liquid.

Here, in the case where the existence of a liquid, the level of the liquid or the surface of the liquid is detected, it is preferable for the nozzles to be irradiated with light, so that light transmitting through the nozzles can be received. This light detection means can be applied to the apparatus for processing a microplate. Here, the "light detecting portion" is a light emitting portion and/or light receiving portion including an irradiation portion that is irradiated with light. The "vicinity of the nozzles" is the degree of closeness in which the state of the liquid inside a nozzle can be detected through the detection of light, and includes cases of contact with the nozzle. It is preferable for the number of straight lines or curves to be smaller than the total number of nozzles provided on the nozzle head. It is more preferably (number of rows+1) or (number of columns+1) of the nozzles. In addition, the same description as for the third invention applies for the "straight lines" and "curves." "Approach" is arrival at a location in the vicinity of the nozzles.

The ninth invention provides a segmented process apparatus for a microplate, wherein the light detecting means includes: one or more comb teeth members in rod form, which extend in the row direction or the column direction and which are correspondingly aligned in the column direction or the row direction so as to come adjacent to one or two nozzle rows or nozzle columns; a support member connected to the one or more comb teeth members at one end and movable relative to the nozzles; and light detecting portions provided in the vicinity of the other end of the comb teeth members in order to optically detect the inside of the nozzles belonging to one or two nozzle rows or nozzle columns adjacent to each other in sequence. The moving path of the light detecting portion is a straight line or a curve, which does not cross the nozzles.

Here, in the case where a nozzle transmits light in order to detect the existence of a liquid, the level of the liquid or the surface of the liquid, the comb teeth members are provided on the two sides of the columns of the nozzles or the rows of the nozzles so as to sandwich them, and it is preferable to provide an irradiation means with one comb teeth member and provide a light receiving means with the other comb teeth member. Accordingly, the number of comb teeth members is (number of rows+1) or (number of columns+1) in this case. Here, in the case where the irradiation means and the light receiving means are provided on the same side so as to measure the reflection from inside a nozzle, the example described for the above magnetic force means in term of the number of nozzles applies as it is. In addition, at least one of the comb teeth members can be inserted between the rows of the nozzles or between the columns of the nozzles, and the direction in which the support member moves is the column direction or the row direction.

The tenth invention provides a segmented process apparatus for a microplate, wherein the nozzle head has an integrated nozzle body where a number of nozzles, which are a part of or all of two or more nozzles set in array are integrated, and the suction and ejection mechanism has two or more suction and ejection elements connected to each of the nozzles of the integrated nozzle body.

Here, "integrated" means a state where collected objects cannot be separated. It is preferable for the nozzles provided on the nozzle head to be aligned in such a manner that the tip of the nozzles is located on the same plane and the axes of the nozzles are parallel. In addition, it is preferable for two or more of the suction and ejection elements in the suction and ejection mechanism to be set in array. Furthermore, it is preferable for the suction and ejection elements to be integrated, so that an integrated body of the suction and ejection elements is formed. In addition, the integrated body of suction and ejection elements may be combined with the integrated body of nozzles, so that an integrated body of nozzles with a suction and ejection mechanism is formed.

In addition, two or more nozzles are integrated in such a manner that portions for storing a liquid are separated with only one wall plate, and thus, the volume for storing a liquid in each nozzle can be increased. In this case, it is necessary for the tip of the nozzles having openings to be integrated, so they can be inserted into the wells in the microplate individually. Here, the integrated body of nozzles can be applied to the apparatus for processing a microplate.

The eleventh invention provides a segmented process apparatus for a microplate, wherein the integrated nozzle body has an integrated nozzle body for attachment where two or more nozzles for attachment are set in array are integrated; and an integrated dispenser tip body where two or more dispenser tips mounted on the nozzles for attachment of the integrated nozzle body for attachment are set in array are integrated, and each of the nozzles for attachment in the integrated nozzle body for attachment is connected to one corresponding dispenser tip in the integrated dispenser tip body. Two or more dispenser tips can be integrated, so that portions for storing a liquid are separated from each other with only one wall plate, and thus, the volume for storing a liquid can be increased.

Here, the integrated body of dispenser tips has an integrated body which is partitioned into two or more sections for storing a liquid set in array connected to the respective nozzles for attachment and can store a liquid inside, and two or more tubules respectively connected to the sections for storing a liquid in the integrated body and having two or more openings at the end for sucking and ejecting a liquid and set in array, the plane having openings at the end of the integrated body of the nozzles for attachment has openings at the tip of the nozzles for attachment set in array, and the surface having openings at the rear of the integrated body of the dispenser tips has openings at the rear of the sections for storing a liquid set in array, and the openings at the tip of the nozzles for attachment and the corresponding openings at the rear of the sections for storing a liquid are connected in a state of close contact. The integrated body of nozzles for attachment is combined with the integrated body of suction and ejection elements, and thus, an integrated body of nozzles for attachment with a suction and ejection mechanism to which a suction and ejection mechanism is attached may be formed.

Here, the "sections for storing a liquid" are partitioned in grid form without being connected to each other through separation walls in thin plate form, and the entirety of the integrated body is in rectangular parallelepiped form, prism form or cube form, for example.

The twelfth invention provides a segmented process method for a microplate including a step of providing a predetermined microplate provided with a number of wells are set in array, one or more nozzle heads provided with a number of nozzles set in array, a suction and ejection mechanism for sucking and ejecting a gas via the nozzles, and a moving means which allows relative movement between the microplate and the nozzle heads, wherein the tips of all of the nozzles provided on each nozzle head are provided in such a manner that the tips can be inserted into the wells in a part of the microplate all together, and the row intervals and column intervals of said nozzles in array are respectively same as the row intervals and column intervals of the wells in array, and the method including a step of positioning nozzles at locations where all of the nozzles provided on the nozzle head can be inserted into the wells in portion of the microplate all together by moving said nozzle head relative to said microplate.

The thirteenth invention provides a segmented process method for a microplate wherein the step of positioning nozzles is carried out in sequence on a number of sub-arrays of wells, which are contained in the microplate, into each of which the tip of all of the nozzles provided on the nozzle head can be inserted all together, and each of the sub-arrays does not include a well overlapping with each other.

Here, it is preferable for each of the number of sub-arrays of wells along the moving path of the nozzle head to contain a solution or a suspension liquid required in the step of the process in accordance with the order of the steps. In addition, it is preferable for the wells containing a solution to be sealed by sticking a sticker on the surface of the microplate in units of sub-arrays of wells. As a result, evaporation and contamination of the reagents can be prevented. In this case, the tips of the dispenser tips make a hole in the sticker, so that the liquid can be sucked up or ejected.

The fourteenth invention provides a segmented process method for a microplate further including the steps of: applying a magnetic field to inside each of the nozzles by moving each of magnets toward each of the nozzles along a straight line or a curve that passes in the vicinity of the nozzles without crossing either of the nozzles; and removing the magnetic field by relatively moving the magnet away from each of the nozzles.

This invention can be applied to a method for processing a microplate having the steps of: providing a predetermined microplate where a number of wells are set in array, one or more nozzle heads where a number of nozzles are set in array, a suction and ejection mechanism for sucking and ejecting a gas via the nozzles, a moving means which makes relative movement possible between the microplate and the nozzle heads, and the tips of all of the nozzles provided on each nozzle head are provided, inserting the tips into some of the wells in the microplate all together, and moving the row intervals and column intervals of the nozzles in array to respectively the same row intervals and column intervals of the wells in array.

The fifteenth invention provides a segmented process method for a microplate, wherein the step of applying a magnetic field to inside each of the nozzles and the step of removing the magnetic field are carried out using a magnetic force means including: one or more comb teeth members in rod form, which extend in the row direction or the column direction and which are correspondingly aligned in the column direction or the row direction so as to come adjacent to one or two nozzle rows or nozzle columns; a support member connected to one or more of the comb teeth members at one end and is movable relative to the nozzles; and the magnets provided in each comb teeth member in locations corresponding to the nozzles belonging to the one or two nozzle rows or nozzle columns adjacent to each other, the magnetic field is applied to each of said nozzles by moving said comb teeth member toward said nozzles, the magnetic field is removed from each of the nozzles by moving the comb teeth member away from the nozzles.

The sixteenth invention provides a segmented process method for a microplate, including the steps of: after the step of positioning nozzles at locations where all of the nozzles provided on the nozzle head can be inserted together, inserting the tip of all of the nozzles provided on the nozzle head into the wells in the microplate all together to perform a certain process; and removing the nozzles from the wells all together.

Here, "processes" include an operation for sucking and ejecting a liquid, separation of magnetic particles through adsorption on the inner wall of the nozzles when applying a magnetic field, stirring through repetition of suction and ejection, washing through repetition of suction and ejection of a washing liquid, measurement of a liquid after suction or ejection through light detection, and re-suspension of magnetic particles through repetition of suction and ejection after removing the magnetic field, for example.

The seventeenth invention provides a segmented process method for a microplate, wherein each of the nozzles provided on the nozzle head has a nozzle for attachment and a dispenser tip detachably attached to the nozzle for attachment, the method including the steps of: attaching or detaching the dispenser tip to or from a part of or all of the nozzles for attachment provided on the nozzle head.

"Attachment" is carried out by lowering the nozzle head toward a tip containing portion which can contain dispenser tips set in array, and by inserting some or all of the nozzles for attachment into the openings for attachment provided at the upper end of the dispenser tips, for example. "Detachment" is carried out by lowering a plate for stroking or a pipe for stroking provided as a tip detaching portion in the nozzle head, for example, in the direction of the axis line of the nozzles for attachment so that some or all of the dispenser tips mounted on the nozzles for attachment are scraped off, for example.

The eighteenth invention provides a segmented process method for a microplate, further including the steps of: detecting the state of the liquid inside the nozzles provided on said nozzle head in sequence by relatively moving a light detecting portion toward each of the nozzles in sequence along a straight line or a curve that passes in the vicinity of each of said nozzles without crossing either of said nozzles.

Effects of the Invention

According to the first and twelfth inventions, even in the case where the number of specimens is small and not all of the wells in a microplate or all of the rows or columns in a microplate are required, a nozzle head where nozzles are set in array so that they can be inserted into a standard, normal microplate and some wells in the microplate together, or a partial standard, normal microplate is used instead of a microplate having a number of rows, a number of columns and intervals between rows and columns in accordance with the number of specimens and a nozzle head that is suitable for the microplate, for example, and thus, a simple process can be made possible at low cost, without using any new type of microplate. In addition, one microplate can be used for various types of objects to be processed and reagents, and therefore, there are many applications for the microplate.

In addition, all of the wells are segmented into a number of regions (corresponding to the below described sub-arrays of wells) in accordance with the number of required steps for one microplate and the number of reagents used, so that all of the regions can be processed together using the nozzle head, and thus, the process can be completed using one microplate. Accordingly, the area occupied by the used microplate, that is to say, the work area, can be made smaller.

In addition, nozzles are set in array in the nozzle head, and therefore, the containers in array are stable and easy to handle, even in the case where the number of wells is small and the wells are containers having a small volume in comparison with the case where a container where wells are aligned in one row or one column is used as a container for containing a necessary reagent. In addition, all of the nozzles and corresponding wells are set in array, and thus, the distance between elements belonging to the matrix is relatively small; that is to say, the dispersion is relatively small, and the elements are concentrated in small area, and therefore, nozzles, wells and other constant temperature apparatuses have excellent heat retaining properties, particularly during the process requiring temperature control, and thus, the elements can be shielded against outside effects and are easy to handle.

According to the second and thirteenth inventions, one microplate has two or more sub-arrays of wells that can accept all of the nozzles provided on the nozzle head, and therefore, in addition to the above described effects, a process can be carried out with one microplate containing two or more types of reagents, and therefore, it becomes possible to handle more reagents without increasing the work area, as compared to the case where a process is carried out with each microplate containing a reagent. In particular, in the case where all of the wells in a microplate can be segmented into a number of sub-arrays of wells corresponding to the number of steps required in the process or the number of reagents used, all of the sub-arrays of wells can be processed together using the nozzle head, and thus, the process can be completed using one microplate.

In addition, a number of sub-arrays of wells in the microplate can allow one nozzle to correspond to two or more wells, and thus, a liquid of which the volume is more than twice that of the liquid that can be handled by one well in each step can be handled by one nozzle for one microplate.

The nozzles are inserted into a number of sub-arrays of wells in the microplate together, liquids are sucked up and ejected together, and the nozzles are removed together, and this is repeated, so that one microplate can handle a number of steps using a number of solutions. Accordingly, a number of steps can be carried out without expanding the work region.

Furthermore, two or more sub-arrays of wells are provided within one microplate as part of the microplate, and these are at a distance from each other of only row intervals and column intervals of the microplate, and therefore, the stability is high and the sub-arrays of wells make contact with each other, unlike in the arrangement of separate microplates having wells in the same number of rows and columns, and thus, the sub-arrays of wells can be aligned efficiently in terms of the space.

In addition, wells that can be handled once by one nozzle head belong to one of the sub-arrays of wells which do not overlap within one microplate and the distance between the sub-arrays of wells only corresponds to the distance between adjacent wells in the microplate, and therefore, all of the solutions required for one process are contained in the sub-arrays of wells, and thus, the distance over which the nozzle head moves before one process is completed is short, and thus, the process can be carried out quickly and efficiently.

According to the third and fourteenth inventions, a magnetic field can be applied inside the nozzles, and therefore, a liquid inside which magnetic particles are suspended is put in the wells of the microplate, so that the magnetic particles are adsorbed on the inner walls of the nozzles when processes, such as separation, stirring, washing and moving, are carried out, and therefore, various processes, including suction and ejection or a liquid, can be carried out. In addition, a magnet is provided in such a manner that it can move toward and away from the nozzles, and thus, a strong magnetic field can be applied to the nozzles, and at the same time, any magnetism which would remain after demagnetization of the electromagnet can be completely removed when a strong magnet is moved away from the nozzles, and thus, a process can be carried out with high reliability.

In addition, the magnet moves along a straight line or a curve that passes through the periphery of the nozzles without crossing them, for example a straight line or curve that lies along a skew line relative to the nozzles. Accordingly, the magnet is not hindered by the nozzles when moving, so that it is possible to apply and remove a magnetic field, and therefore, it is not necessary to secure a space between nozzles taking the distance over which the magnet moves into account on the basis of the effective distance of the magnetic field created by the magnet, and it is sufficient to secure a space between nozzles on the basis of the size of the magnet that passes through. Accordingly, nozzles the inside of which a magnetic force can be applied can be integrated with high density.

According to the fourth and fifteenth inventions, in addition to the effects in the third and fourteenth inventions, a magnetic field can be applied to and removed from all of the nozzles together with ease and without failure, by providing a mechanically simple structure with a simple operation, by moving comb teeth members where magnets are provided at distances of the row intervals and column intervals of the nozzles relative to the nozzles so that magnets move toward and away from the nozzles set in array.

According to the fifth and sixteenth inventions, the operation for insertion and removal of the tips of all of the nozzles in the nozzle head in a number of sub-arrays in one microplate is repeated, and thus, a sequence of processes including a number of processing steps can be carried out continuously, using one nozzle head per microplate, and therefore, the efficiency in the process per work area is high, and the efficiency of the work is high, with high reliability and ease.

According to the sixth invention, the solutions or suspension liquids required for the respective steps in the process are contained in the order of the steps along the moving path of the nozzle head. Accordingly, the distance over which the nozzle head moves is limited to one microplate, and thus, the efficiency of work is high. In addition, the process can be carried out continuously within one microplate using one nozzle head with high reliability and ease.

According to the seventh and seventeenth inventions, the necessary number of dispenser tips depending on the number of wells arranged in the microplate or the size of the containers such as reagent tanks, can be attached to and/or detached from the nozzle head automatically instead of manually, and therefore, there are many applications, and in addition, various processes can be automated in sequence while preventing cross-contamination without fail. In particular, in the case where the volume of the reagents used is small, the area of the opening of the reagent tank is made small, so that the number of dispenser tips that can be inserted is limited, so that the liquid is deep, and thus, it is easy to suck and eject the liquid.

According to the eighth and eighteenth inventions, the light detecting portion is not provided with individual nozzles, and it is moved close to each nozzle in sequence along a straight line or a curve that does not cross the nozzles, so that the state of the liquid inside the individual nozzles can be detected. Accordingly, it is not necessary to provide a light detecting portion in the periphery of individual nozzles, and it is not necessary to secure a distance over which light does not have any effect between the nozzles, and therefore, a process can be carried out with high reliability for constant amounts of liquid at low cost and without affecting the degree of integration of the nozzles, simply by securing a space between nozzles through which the light detecting portion can move.

According to the ninth invention, in addition to the effects in the eighth and eighteenth inventions, the comb teeth members provided with a light detecting portion move relative to the nozzles, so that the light detecting portion moves toward and away from the respective nozzles set in array in sequence, and the inside of the respective nozzles can be measured in sequence with ease and without fail and through a simple operation, by providing a simple mechanical structure.

According to the tenth invention, nozzles are integrated so that they can be partitioned with only one separation wall, and therefore, the thickness of the nozzles and the space between nozzles need not be great, as compared to the case where individual nozzles are provided, and thus, the nozzles can be aligned with high density and without any spaces, so that the effective volume of the liquid that can be stored in one nozzle per work area can be increased. Accordingly, the length of the nozzles can be reduced in the axial direction, and thus, nozzles for the same volume can be formed in a small area as a whole. In addition, two or more nozzles can be provided in predetermined locations without failure, and thus, a highly reliable process can be carried out.

According to the eleventh invention, dispenser tips can be partitioned with only one separation wall, by integrating the dispenser tips, and therefore, the thickness of the dispenser tips and the space between the dispenser tips need not be great, as compared to the case where individual dispenser tips are mounted in the nozzles for attachment, and thus, the dispenser tips are provided with high density and without spaces in between, and the effective volume of the liquid that can be stored in one dispenser tip per work area can be increased. Accordingly, the length of the dispenser tips can be reduced in the axial direction, and dispenser tips for the same volume can be formed in a smaller area. In the case where the inner diameter of portions for storing a liquid in a single dispenser tip is approximately 6 mm for a standard, normal microplate with 96 wells, for example, the length of the section for storing a liquid needs to be 88.5 mm, while there is no waste of space between the tips when integrated, and therefore, in the case where the diameter of the inner walls of the section created as a round hole is approximately 8 mm, for example, the length of the section for storing a liquid may be as short as 49.8 mm. In addition, the intervals between dispenser tips can be made constant, so that the axes of the dispenser tips can be aligned parallel to each other without failure, and a highly reliable nozzle head can be provided.

BEST MODE FOR CARRYING OUT THE INVENTION

Next, the segmented process apparatus for a microplate and the segmented process method for a microplate according to the embodiments of the present invention are described with reference to the drawings.

FIG. 1 is a perspective diagram schematically showing a nozzle head 12 portion of the segmented process apparatus for a microplate 10 according to the first embodiment of the present invention. The segmented process apparatus for a microplate 10 has a nozzle head 12 where nozzles for attachment (not shown), which are 16 nozzles aligned in 4 rows×4 columns here, and dispenser tips 14 mounted on the nozzles for attachment are set in array having row intervals and column intervals which are the same as in standard, normal microplates (not shown) with 96 wells in 12 rows×8 columns, where a number of wells are set in array with row intervals (column intervals) of 9 mm, that is to say, with standard, normal row intervals (standard, normal column intervals), suction and ejection mechanisms (16, 18, 28, 30, 32, 34, 36) provided in the nozzle head 12 for sucking and ejecting a gas via the nozzles, and a moving means (partly shown) which makes relative movement between the standard, normal microplate and the nozzle head 12 possible.

Furthermore, the nozzle head 12 has a magnet in comb teeth form 20, which is a magnetic force means for applying a magnetic field inside the dispenser tips 14, a light detecting portion in comb teeth form 22, which is a light detecting means for detecting the state of the liquid inside the dispenser tips 14, and a tray 24 inserted between the dispenser tips 14 and the microplate beneath the tips in order to prevent the liquid from dripping from the dispenser tips 14.

The suction and ejection mechanism (16, 18, 28, 30, 32, 34, 36) have sixteen cylinders 16 which are respectively connected to the nozzles for attachment (not shown) and mounted dispenser tips 14 and set in array so as to protrude down from the plate for aligning nozzles 26, plungers 18 inserted into the cylinders 16 in such a manner as to be slidable, a plate for driving the plungers 28 which is connected to the sixteen plungers 18, two actuators in pillar form 30 which are connected to the plate for driving the plungers 28 so as to drive the plate for driving the plungers 28, as well as the plungers 18, all together in the up-down direction (direction of z axis), a nut which is connected to the actuator 30, screwed on a ball screw 34 in order to drive the actuator 30 in the up-down direction, and translates in the up-down direction as a ball screw 34 rotates, and the ball screw 34, which is driven by a motor for sucking and ejecting a liquid 36 so as to rotate. A nozzle head support frame 37 formed in approximately box form is provided so as to cover these suction and ejection mechanisms, supports the motor for sucking and ejecting a liquid 36 and the plate for aligning nozzles 26, and supports the actuator 30 in such a manner that it is movable up and down.

The nozzle head support frame 37 has a top plate 38 provided at the upper end, side plates 39 and 40 which are long in the up-down directions and cover the left and right sides in the Figure, a rear plate 41 which is long in the up-down directions and covers the rear side, and a bottom plate 43 which is long in the left-right directions and attached so as to face the transmission path of the nozzle head 12 on the bottom side. In addition, the side plate 40 is provided with a long hole 42, and a connection member (not shown) connected to a Z axis moving mechanism for moving the nozzle head 12 along the nozzle head support frame 37 in the up-down directions is provided so as to penetrate through the long hole 42.

FIG. 2 shows the details of the portion of the segmented process apparatus for a microplate 10 shown in FIG. 1 where the nozzle head 12 is located. The connection member is connected to a ball screw 78, which is attached to a plate 80 provided in the nozzle head support frame 37 so as to be rotatable, and to a nut (not shown) screwed on the ball screw 78 as the Z axis moving mechanism.

The nozzle head support frame 37 supports the Z axis moving mechanism connected to the nozzle head 12, but does not move in the direction of the Z axis, and is connected to the ball screw 74 provided so as to have an axis in the direction of the X axis, which works as an X axis moving mechanism (X axis is in the direction of the rows of the nozzles in the nozzle head 12), and to a nut 76 screwed on this. Furthermore, the nozzle head support frame 37, the Z axis moving mechanism and the X axis moving mechanism are attached to a Y axis moving mechanism (Y axis is in the direction of the columns of the nozzles in the nozzle head 12), not shown, provided so as to have an axis in the direction of the Y axis, and the Z axis moving mechanism, the X axis moving mechanism and the Y axis moving mechanisms correspond to the moving means.

As shown in FIG. 2, the dispenser tips 14 have large diameter portions 44 with openings for attachment through which the portions are or can be mounted in the nozzles for attachment (not shown), small diameter portions 46 with openings 48 through which a liquid can enter and be dispensed through the suction and ejection of the gas provided at the ends, and moving portions 50 approximately in funnel form.

As shown in FIGS. 2 and 3, the above describe magnetic force means is a magnet in comb teeth form 20 which is provided so as to be movable relative to the dispenser tips 14 which work as the nozzles, and three comb teeth members 84 in rod form aligned in the direction of the columns so that they can come close to the rows of one or two dispenser tips (nozzles) extending in the direction of the X axis (or in the direction of the rows), a support member 52 which can move in the direction of the rows and is connected to the ends of the three comb teeth member 84, and a number (four in this example) of permanent magnets 58 provided in the respective comb teeth members 84 in such locations as to correspond to the respective dispenser tips 14 belonging to the one or two adjacent dispenser tip columns are aligned in the three comb teeth members 84 respectively in such a manner as to sandwich the non-magnetic members 82 with row intervals corresponding to the spaces between the dispenser tips 14 mounted in the nozzles for attachment (not shown).

As a result, the permanent magnets 58 are provided so as to be movable towards and away from the respective dispenser tips 14, and the comb teeth members 84 can move along a straight line which does not cross the dispenser tips 14. In the case where the comb teeth members 84 approach the dispenser tips 14 so as to apply a magnetic force, two of the three at both ends are arranged in the direction of the rows so as to be adjacent to the four dispenser tips from the outside, and the middle one is inserted in the center space between the rows of dispenser tips 14 in the nozzle head 12 and arranged in the direction of the rows. Accordingly, in the case where a magnetic field is applied to the dispenser tips, that is to say, in a state where the comb teeth members are in close proximity to the dispenser tips 14, every two dispenser tips are sandwiched by the comb teeth members 84.

The support member 52 is connected to a guide member 54, and the guide member 54 is engaged with a guide rail 56 provided on the bottom plate 43 in the nozzle head support frame 37 so as to run in the direction of the X axis (direction of the rows) and provided so as to be movable in the direction of the rows along the guide rail 56.

As shown in FIGS. 2 and 3, the light detecting portion in comb teeth form 22 is provided. The light detecting portion in comb teeth form 22 has the five comb teeth members 62 in rod form which extend in the direction of the X axis (direction of the rows) so as to be movable relative to the nozzles, can move close one or two rows of dispenser tips 14, and are aligned in the direction of the Y axis (direction of the columns), a support member 67 connected to one end of the five comb teeth members 62, and an tip portion of an optical fiber 64 provided in a hole 60 in the vicinity of the other end of the comb teeth members 62 as a light detecting portion in order to optically and sequentially detect the inside of the dispenser tips 14 belonging to one row of dispenser tips to which the optical fiber is adjacent. An tip of an optical fiber 64, which is a light emitting portion, is provided in the hole 60 of one of the two teeth comb member 62 on the two sides provided so as to sandwich one row of the dispenser tips 14, and an tip of an optical fiber, which is a light receiving portion, is provided in the hole 60 of the other comb teeth member so that the amount of light that is emitted from the optical fiber 64, which is a light emitting portion, and that transmits the dispenser tips 14 is detected.

The optical fiber 64 transmits light received through the hole 60 to an analyzing portion having a photoelectric element, such as a photoelectrical amplifier (not shown).

The light detecting portion in comb teeth form 22 is connected to a guide member 66, and the guide member 66 engages with a guide rail 68 which is provided on the bottom plate 43 on the nozzle head support frame 37 so as to run in the direction of the X axis (direction of the rows), and thus, are provided so as to be movable in the direction of the rows along the guide rail 68.

The tray 24 is connected to a guide member 70, and the guide member 70 engages with a guide rail 72 provided on the bottom plate 43 in the nozzle head support frame 37 so as to run in the direction of the X axis and are provided so as to be movable in the direction of the X axis along the guide rail 72, and when the tray moves beneath the openings 48 at the ends of the dispenser tips 14 so as to receive liquid dripped through the openings 48, liquid can be prevented from dripping.

FIG. 4 is a plan diagram showing the entirety of the segmented process apparatus for a microplate 10.

Here, such a state is shown that the nozzle head 12 is provided on a stage 85 on which a group of various containers is provided. The stage 85 has a container which is partitioned into 16 sections in array of 4 rows×4 columns with intervals between the rows and the columns of 9 mm, which is the standard, normal intervals between rows and columns, so that all the ends of the dispenser tips 14 aligned in the nozzle head 12 can be inserted together and which can contain a liquid, and a cooler 86 and a heater 88 for a constant temperature incubation each having a cooling means and a heating means, such as a Peltier element. The cooler 86 and the heater 88 correspond to the partially standard, normal microplate. In addition, the stage 85 has a thermal cycler 90 for amplifying PCR having holes arranged in array of 4 rows×4 columns with intervals of rows and columns that makes it possible for all the dispenser tips 14 aligned in the nozzle head 12 to be inserted together.

Furthermore, the stage 85 has a specimen container 92 in array of 4 rows×4 columns having intervals of rows and columns of 9 mm so that the specimens of 16 people can be contained, a reagent tank containing rack 94 for containing reagent tanks, each of which stores distilled water A, magnetic particle suspension liquid B and reagents C to H required for processing, a standard, normal microplate 96 having 96 deep wells 97 in 12 rows×8 columns of which the volume is approximately 2,000 µl with the intervals of the rows and columns of 9 mm (corresponding to the standard, normal intervals between the rows and the columns) on which a segmented process is carried out according to the present embodiment, a standard, normal tip containing portion 98 with the intervals of the rows and columns of 9 mm which can contain 96 dispenser tips 14 in 12 rows×8 columns, tip disposal chute 102 through which used dispenser tips 14 are discharged to the outside after being detached from the nozzle head 12, and a funnel for waste 104 for collecting liquid waste discharged from the dispenser tips 14. The specimen container 92 corresponds to the partial standard, normal microplate. The standard, normal microplate 96 has six well sub-arrays 96a to 96f made up of wells in 4 rows×4 columns into each of which all of the tips of the dispenser tips 14 provided in the nozzle head 12 can be inserted together and which do not overlap with each other.

Here, though not shown, the segmented process apparatus for a microplate 10 according to the present embodiment has the suction and ejection mechanism, a moving means, a magnetic force means and a control portion for controlling the operation of the light detecting means, and the control portion has an information processing apparatus having a memory for storing programs and data for the CPU and operation in accordance with the instructions, a display portion, such as a display, for displaying the operational state, the data of instructions and orders, input data and data of the process results, an input means made up of a keyboard, a mouse and the like to input instructions, orders and data, and an output means, such as a printer, an external memory or a communication means, for outputting the data of the process results.

Next, the operation of the segmented process apparatus for a microplate 10 according to the first embodiment is described with reference to FIG. 4 by citing an example of a process for extracting nucleic acid, such as DNA, mRNA and rRNA, from 16 specimens, such as blood collected from 16 people, contained in the specimen container 92.

The nozzles for attachment in the nozzle head 12 are moved predetermined locations of the tip containing portion 98, and then lowered together so that a predetermined number of dispenser tips 14 are newly mounted in the nozzles for attachment, and after that the nozzle head 12 is moved to the reagent tank containing rack 94, dispenser tips 14 mounted in the nozzle head 12 are used after being moved from predetermined reagent tanks in the reagent tank containing rack 94, and the reagents C to H are sucked so that a predetermined amount of the reagents is put in the 16 wells belonging to the well sub-arrays 96a to 96f in advance. Here, the "predetermined number" is the number of dispenser tips 14 mounted in the nozzle head 12 and depends on the size of the reagent tanks contained in the reagent tank containing rack 94, and thus, the number of nozzles for one row in the nozzle head 12, that is to say, four for each of the reagents B to H, and the number of all the nozzles on the nozzle head 12, that is to say, 4 rows×4 columns=16, for the reagents A and B.

The well sub-array 96a in the standard, normal microplate 96 contains protenase K (1-40 mg/ml) for dissolving cells (reagent C), the well sub-array 96b contains guanidine HCl (4-8 M) for dissolving cells, and a solution of detergents (reagent D), the well sub-array 96c and the well sub-array 96d contain a mixed solution of alcohol (for example, 20-60% of isopropyl alcohol, ethanol) (reagent E), a salt (for example, 0.5-2.5 M of $CH_3COONH_4$) (reagent F) and a water soluble polymer (for example, 1-10 wt % of PVA, PEG) (reagent G), the well sub-array 96e contains a dissociation liquid of 1-10 Mm of Tris-HCl (pH 7-8) (reagent H), and the well sub-array 96f is empty. Here, reagent A is nucleus free water and reagent B is a suspension liquid of magnetic particles having a functional group, such as a hydroxide group or a carboxyl group, on the surface.

The nozzle head 12 is moved by a moving means so as to be placed in such a location that all the tips can be inserted into the wells of 4 rows×4 columns in the specimen container 92, and all the dispenser tips 14 are inserted together so that the 16 specimens are sucked at the same time. Next, the nozzle head 12 is moved by the moving means so as to be placed in such a location that all the dispenser tips 14 can be inserted together into the wells in 4 rows×4 columns in the well sub-array 96a on the standard, normal microplate 96, and all the dispenser tips 14 are inserted together into the wells so that the specimens are ejected. Suction and ejection are repeated in order to stir the liquid, and the stirred suspension liquid is sucked into the dispenser tips 14, and after that all the dispenser tips 14 are pulled out together from the well sub-array 96a.

Next, the moving means is used to place the nozzle head 12 in such a state that the dispenser tips 14 can be inserted into the wells in the well sub-array 96b, and all the dispenser tips 14 are inserted into the wells in the well sub-array 96b so that the suspension liquid contained in the dispenser tips 14 is ejected, and after that suction and ejection are repeated in order to stir the liquid so that the cell walls of the cells included in the specimens are dissolved and DNA is extracted from the cells in the liquid.

Next, all of the dispenser tips 14 are removed from the sub-array of wells 96b together in such a state that the suspension liquid including DNA, as described above, is sucked into the dispenser tips 14, and the nozzle head 12 is moved using the moving means, so that it is in such a location that the dispenser tips 14 can be inserted into the wells of the sub-array of wells 96c, and all of the dispenser tips 24 are inserted together into the wells of the sub-array of wells 96c, so that the suspension liquid contained within the dispenser tips 14 is ejected, and the mixed liquid and DNA are stirred together, and after that, the dispenser tips 14 are removed from the sub-array of wells 96c without any suspension liquid being sucked up into the dispenser tips 14, the used dispenser tips 14 are detached from the nozzles for attachment, so that the dispenser tips 14 are contained in predetermined locations in the tip containing portion 98, new dispenser tips 14 are mounted in the nozzles for attachment, and after that, the dispenser tips are moved into reagent tanks in the reagent tank containing rack 94 containing the reagent B is using the moving means, so that the dispenser tips 14 are all inserted together and the magnetic particle suspension liquid is sucked up. The nozzle head 12 is moved to the sub-array of wells 96c, and the dispenser tips 14 are all inserted into the wells together, and the magnetic particle suspension liquid is ejected, and after that, suction and ejection are repeated, in order to mix the liquid, so that DNA included in the liquid combines with the magnetic particles.

When the dispenser tips 14 are inserted into the sub-array of wells 96c so as to suck or eject the liquid, the nozzle head 12 is located at such a level in the direction of the z axis (up-down direction) that the small diameter portions 46 of the dispenser tips 14 are adjacent to the three comb teeth members 84 of the magnet in comb teeth form 20 provided on the bottom plate 43. Thus, the comb teeth members 84 are moved forward in the direction of the rows (direction of X axis), so that the permanent magnets 58 respectively provided in the comb teeth members 84 move close to the dispenser tips 14, and thus apply a magnetic field to the dispenser tips 14.

Then, the magnetic particles combined with the DNA are adsorbed and separated from the inner walls of the small diameter portions 46 of the dispenser tips 14 as a result of the magnetic field when the suspension liquid is sucked up and ejected. Next, the dispenser tips 14 are removed from the sub-arrays of wells 96c, in such a state that the magnetic particles are adsorbed, and the nozzle head 12 is moved to the sub-array of wells 96d together with the magnet in comb teeth form 20 by the moving means, so that the dispenser tips 14 are inserted into the wells together, and suction and ejection of the washing liquid contained within the wells of the sub-array of wells 96d are repeated. At this time, the magnetic particles remain adsorbed on the inner walls of the dispenser tips 14 as a result of the magnetic field applied by the magnetic force means. As a result, magnetic particles with which DNA is combined are washed, so that foreign elements other than the DNA combined with the magnetic particles remain within the wells in the sub-array of wells 96d.

Next, the dispenser tips 14 are removed from the sub-array of wells 96d with the magnetic particles remaining adsorbed on the inner walls and residue remaining within the wells, and the nozzle head 12 is moved to the sub-array of wells 96e by the moving means together with the magnetic force means 20, so that the dispenser tips 14 are all inserted into the wells together, and suction and ejection of the dissociation liquid contained in the respective wells in the sub-array of wells 96e are repeated while the magnetic force means 20 keeps applying a magnetic field, so that DNA combined with the magnetic particles is dissociated from the magnetic particles and contained in the dissociation liquid.

The nozzle head 12 on which the dispenser tips 14 for adsorbing magnetic particles are mounted is moved, so that the dispenser tips 14 are detached from the nozzle head 12, and after that, the nozzle head is moved to the tip containing portion 98, and new dispenser tips 14 are mounted. The nozzle head 12 is moved to the sub-array of wells 96e, and the dispenser tips 14 are all inserted into the wells, so that the liquid containing DNA is sucked up, and moved to a thermal cycler to be amplified by PCR, for example. Alternatively, the nozzle head may be moved to the cooler 86 or the heater 88 so that various processes can be carried out. The thus gained product is contained in the sub-array of wells 96f. Accordingly, a sequence of processes can be completed using the standard, normal microplate 96. The path through which the nozzle head 12 moves during this process is a path starting from the sub-array of wells 96a and going through the sub-arrays of wells to the sub-array of wells 96f in sequence in alphabetical order.

FIG. 5 shows a group of containers in the segmented process apparatus for a microplate 100 according to the second embodiment. The segmented process apparatus for a microplate 100 uses the same nozzle head 12 as the segmented process apparatus for a microplate 10 according to the first embodiment, where nozzles are aligned in 4 rows×4 columns.

The stage 106 in the segmented process apparatus for a microplate 100 according to the second embodiment has six standard, normal microplates 108 for inducing reaction having 96 deep wells 109 in 12 rows×8 columns with a volume of approximately 2000 μl and intervals of rows and columns of 9 mm (corresponding to standard, normal intervals for rows and columns), into which the tips of all of the dispenser tips 14 aligned in the nozzle head 12 can be partially inserted together, and inside which a liquid can be contained, so that the segmented process according to the present embodiment can be carried out, three standard, normal tip containing portions 110 with intervals of rows and columns of 9 mm which can contain 96 dispenser tips 14 for inducing reaction in 12 rows×8 columns, and a standard, normal tip containing portion 111 with intervals of rows and columns of 9 mm which can contain 96 dispenser tips 14 for dispensing a reagent in 12 rows×8 columns.

Furthermore, the stage 106 provides a standard, normal microplate which is partitioned into 96 deep wells in array of 12 rows×8 columns where the intervals of rows and columns are the standard, normal intervals for rows and columns of 9 mm, and the tips of all of the dispenser tips 14 aligned in the nozzle head 12 can be inserted together, and which can contain a liquid, and has a heater 112 having a Peltier element or the like, a cooler 113 made of a thermal cycler having holes in array of 12 rows×8 columns with the same intervals for rows and columns as in the above, into with the tips of all of the dispenser tips 14 aligned in the nozzle head 12 can be inserted together, a reagent tank rack 14 for containing reagent tanks, a standard, normal microplate 115 having 96 wells for containing specimens, a tip disposal chute 116 for removing and discharging dispenser tips to the outside for disposal, and a funnel for liquid waste 118 through which liquid waste discharged from the dispenser tips 14 is collected.

FIG. 6 shows three types of nozzles: 120, 144 and 150 according to the third embodiment.

FIG. 6(a) shows a nozzle 120 for a standard, normal microplate having 96 wells in 12 rows×8 columns with intervals of rows and columns of 9 mm (corresponding to standard, normal intervals for rows and columns), and the intervals of rows and columns between the dispenser tips 124 in the case where the tips are mounted in the nozzles for attachment 122 in the nozzle head are also 9 mm.

The nozzles for attachment 122 have cylinders 126 provided with plungers 128, which are slidable inside, pipes 132 having an inner diameter slightly greater than the outer diameter of the cylinders 126 provided around the cylinders 126 and engaged with them, and tip attaching portions 130 on which the dispenser tips 124 are mounted.

The dispenser tips 124 have large diameter portions 134 having openings for attachment 142 through which the tip attaching portions 130 of the nozzles for attachment 122 can be mounted, small diameter portions having openings 138 through which a liquid can go in and out through suction and ejection of the gas provided at the end, and moving portions 140 approximately in funnel form. In addition, a number of protrusions 143 are provided on the external peripheral surface in the rear of the large diameter portions 134 in the direction of the axis.

The pipes 132 are provided in such a manner as to be movable in the direction of the axis, and at the same time, can be used as tip detaching portions for detaching the dispenser tips 124 on the nozzles for attachment 122, where the inner diameter of the pipes 132 is greater than the outer diameter of the cylinders 126 but smaller than the outer diameter of the large diameter portions 134 of the dispenser tips 124, or the length of section crossing the rigid lines of the protrusions 143.

Here, FIG. 6(b) shows a nozzle 144 for a standard, normal microplate having 384 wells in 24 rows×16 columns with intervals of rows and columns of 4.5 mm (corresponding to standard, normal intervals for rows and columns), which is formed of a nozzle for attachment 146 and a dispenser tip 148, and the intervals of rows and columns between the dispenser tips 148 mounted in the nozzles for attachment 146 in the nozzle head are also 4.5 mm.

Likewise, FIG. 6(c) shows a nozzle 150 for a standard, normal microplate having 1536 wells in 48 rows×32 columns with intervals of rows and columns of 2.25 mm (corresponding to standard, normal intervals for rows and columns), which is formed of a nozzle for attachment 152 and a dispenser tip 154, and the intervals of rows and columns between the dispenser tips 154 in case where dispenser tips 154 are mounted in the nozzles for attachment 152 in the nozzle head are also 2.25 mm.

FIG. 7 shows dispenser tips 124 to be mounted on the nozzle head 156, where the nozzles for attachment 122 in 4 rows×4 columns are aligned with the standard, normal intervals for rows and columns of 9 mm, in order to carry out a segmented process on a standard, normal microplate having 96 wells set in array of 12 rows×8 columns, a magnet in comb teeth form 158, which is a magnetic force means for applying a magnetic field to the dispenser tips 124, and a microplate 166 having 16 wells 168 in 4 rows×4 columns which corresponds to a partial standard, normal microplate of the standard, normal microplate (that is to say, the intervals and rows and columns are the same as the standard, normal intervals of rows and columns for 96 wells).

The magnet in comb teeth form 158 has two comb teeth members in rod form 160 extending in the direction of the rows and aligned in the direction of the columns so as to be movable to the vicinity of two rows of dispenser tips, a support member 162 at one end of which the comb teeth members 160 are connected, which is provided so as to be movable relative to the dispenser tips 124 in the direction of the rows, and magnets 164 provided in the respective comb teeth members 160 in such a location as to correspond to the dispenser tips 124 belonging to the two adjacent rows of dispenser tips. Accordingly, as shown in FIG. 7(b), the comb teeth members 160 are inserted in the spaces between the first row of dispenser tips and the second row of the dispenser tips, as well as between the third row of dispenser tips and the fourth row of dispenser tips, in order to apply a magnetic field to the dispenser tips 124 when in the proximity thereof.

FIG. 8 shows dispenser tips 148 to be mounted on the nozzle head 170, where nozzles for attachment 146 are aligned on the standard, normal microplate having 384 wells in 24 rows×16 columns with intervals of rows and columns of 4.5 mm (corresponding to standard, normal intervals for rows and columns in accordance with the number of wells) in 12 rows×8 columns, a magnet in comb teeth form 172, which is a magnetic force means for applying a magnetic field to the dispenser tips 148, and a microplate 180 having 96 wells 182 in 12 rows×8 columns corresponding to a partial standard, normal microplate of the standard, normal microplate (with intervals of rows and columns corresponding to standard, normal intervals for rows and columns of 4.5 mm).

The magnet in comb teeth form 172 has six comb teeth members 174 in rod form extending in the direction of the rows and aligned in the direction of the columns, so that they can be adjacent to two rows of dispenser tips on both sides, a support member 178 at one end of which the six comb teeth members 174 are connected, which is provided in such a manner as to be movable relative to the dispenser tips 148 in the direction of the rows, and magnets 176 provided for the respective comb teeth members 174 in such a location as to correspond to the dispenser tips 148 belonging to two adjacent rows of dispenser tips. Accordingly, as shown in FIG. 8(b), the comb teeth members 174 are inserted in the space between the first row of dispenser tips and the second row of dispenser tips, between the third row of dispenser tips and the fourth row of dispenser tips between the eleventh row of dispenser tips and the twelfth row of dispenser tips in the case where a magnetic field is applied when in the proximity thereof.

FIG. 9 shows a scheme for detaching dispenser tips 124 according to the second embodiment. The operation of detaching the mounted dispenser tips 124 from the 16 nozzles for attachment 122 on the nozzle head 156 using the pipes 132 in the tip detaching portion is shown.

FIG. 9(a) shows a state where dispenser tips 124 are mounted on the nozzles for attachment 122. In FIG. 9(b), the pipes 132 lower so that the bottom end of the pipes 132 makes contact with the end of openings for attachment 142 at the upper end of the dispenser tips 124, and when the pipes lower further in this state, as shown in FIG. 9(c), the 16 dispenser tips 124 are collectively attached from the nozzles for attachment 122.

FIG. 10 shows another scheme for detaching dispenser tips 124 according to the second embodiment.

As shown in FIG. 10(a), the nozzle head 184 using the scheme has nozzles for attachment 123 aligned in 4 rows×4 columns, a plate for detachment 186 where through holes 187, of which the inner diameter is greater than the outer diameter of the tip attaching portions 130 of the nozzles for attachment 123, that is, the tip detaching portions, and smaller than the outer diameter of the edge of the openings for attaching the dispenser tips 124, are set in array of 4 rows×4 columns, and four supports 188 which support the plate for detachment 186 from the above in the four corners and are movable in the direction of the axis of the dispenser tips 124, and the nozzles for attachment 123 are provided in such a state that the tip attaching portions 130 of the nozzles for attachment 123 are inserted and penetrate through the through holes 187 from above the plate for detachment 186, and the dispenser tips 124 are mounted at the tip of the tip attaching portions 130 that penetrate through the through holes 187 by engaging the openings for attachment 142 with the end. In the nozzles for attachment 123, no movable pipes 132 are provided in the cylinders 127.

As shown in FIG. 10(b), in the case where the dispenser tips 124 are removed from the nozzles for attachment 123, the plate for removal 186 lowers in the direction of the axis of the dispenser tips 124 together with the supports 188. Thus, when it further lowers in such a state that the ends on the lower surface of the through holes 187 make contact with the ends of the openings for attachment 142 at the upper ends of the dispenser tips 124, as shown in FIG. 10(c), the 16 dispenser tips 124 are all removed from the nozzles for attachment 123 together.

FIG. 11 shows the nozzle head 190 according to the fourth embodiment. The same symbols as in FIGS. 6(a) and 7 indicate the same components, and the descriptions thereof are omitted. In the nozzle head 190, nozzles for attachment 129 are set in array in 4 rows×4 columns, and dispenser tips 124 are mounted at the tips of the nozzles for attachment 129. The nozzles for attachment 129 are provided with pipes 194 connected to the inside of the cylinders 192 on the bottom side of the cylinders 192 where plungers 128 are provided so as to be slidable. As a result, a change in the pressure within the dispenser tips 124 and the cylinders 192 can be detected. Therefore, whether or not the liquid is running short, whether or not there is a liquid, and whether the suction and ejection operations are normal or abnormal can be determined, and thus, a highly reliable process can be carried out.

FIG. 12 shows an example of a segmented process for a microplate according to the present embodiment.

FIG. 12(*a*) shows a standard, normal microplate 200 having 96 wells 202 in 12 rows×8 columns with standard, normal intervals of rows and columns of 9 mm and a nozzle head 204 having nine nozzles 205 set in array in 3 rows×3 columns with intervals of rows and columns. The standard, normal microplate 200 has six well sub-arrays 206 made up of nine wells 202 in 3 rows×3 columns and three well groups made up of six wells 202 in 3 rows×2 columns.

FIG. 12(*b*) shows the standard, normal microplate 200 and a nozzle head 208 where 12 nozzles 205 are set in array in 3 rows×4 columns. In the standard, normal microplate 200, all the wells 202 in the standard, normal microplate 200 are segmented into six well sub-arrays 209 having 12 wells 202 in 3 rows×4 columns.

FIG. 12(*c*) shows the standard, normal microplate 200 and a nozzle head 210 where 16 nozzles 205 are set in array in 4 rows×4 columns. In the standard, normal microplate 200, all the wells 202 in the standard, normal microplate 200 are segmented into six well sub-arrays 211 having 12 wells 202 in 3 rows×4 columns.

FIG. 12(*d*) shows the standard, normal microplate 200 and a nozzle head 212 where 25 nozzles 205 are set in array in 5 rows×5 columns. The standard, normal microplate 200 has two well sub-arrays 213 made up of 25 wells 202 in 5 rows×5 columns, a well group made up of ten wells 202 in 2 rows×5 columns, a well group made up of six wells 202 in 2 rows×3 columns, and two well groups made up of 15 wells 202 in 5 rows×3 columns.

FIG. 12(*e*) shows the standard, normal microplate 200 and a nozzle head 215 where 24 nozzles 205 are set in array in 6 rows×4 columns. In the standard, normal microplate 200, all the wells 202 in the standard, normal microplate 200 are segmented into four well sub-arrays 216 made up of 24 wells 202 in 4 rows×6 columns.

FIG. 12(*f*) shows the standard, normal microplate 200 and a nozzle head 218 where 48 nozzles 205 are set in array in 6 rows×8 columns. In the standard, normal microplate 200, all the wells 202 in the standard, normal microplate 200 are segmented into two well sub-arrays 220 made up of 48 wells 202 in 6 rows×8 columns.

FIG. 13 shows the nozzle head 223 according to the fifth embodiment. The nozzle head 223 corresponds to a standard, normal microplate having 96 wells in 12 rows×8 columns with the standard, normal intervals of rows and columns of 9 mm. The nozzle head 223 has a dispenser tip integrated body 226 where 16 dispenser tips are integrated and set in array in 4 rows×4 columns with intervals of rows and columns of 9 mm and a nozzle for attachment integrated body 224 with a suction and ejection mechanism, where a nozzle for attachment integrated body where 16 nozzles for attachment are integrated and set in array in 4 rows×4 columns with intervals of rows and columns, and a suction and ejection element integrated body where 16 suction and ejection elements 231 connected to the respective nozzles for attachment are integrated and set in array in 4 rows×4 columns with intervals of rows and columns, are combined.

The dispenser tip integrated body 226 has a storage integrated body 236 which is partitioned into 16 storage sections 224 set in array in 4 rows×4 columns with intervals of rows and columns of 9 mm by wall plates 245 in grid form, which are respectively connected to the suction and ejection element 231 through the rear surface with openings 227, and which can store a liquid inside, and 16 tubules 238 connected respectively to the storage sections 244 of the storage integrated body 236 via the moving portions 242 approximately in funnel form, aligned so as to protrude beneath in array of 4 rows×4 columns having intervals of rows and columns of 9 mm and 16 openings 240 through which a liquid can be sucked and ejected from sections set in array at the end, and formed so as to be narrower than the storage sections 244. Protrusions extending in the horizontal direction and protruding outwards are provided on the upper side of the two facing outer sides of the storage integrated body 236. On the rear surface with openings 227, the openings at the rear end of the storage sections 244 of the respective dispenser tips are set in array.

The nozzle for attachment integrated body 224 with a suction and ejection mechanism is connected to the openings on the rear end surface 227 of the dispenser tip integrated body 226 on the end surface with openings 229. The nozzle for attachment integrated body 224 with the suction and ejection mechanism has 16 long holes 230 having an inner wall surface in cylindrical form provided in approximately rectangular parallelepiped block 228 and aligned in 4 rows×4 columns, 16 plungers 232 provided within the long holes 230 so as to be slidable and aligned in 4 rows×4 columns, and a plate 233 connected to the upper end of 16 of the plungers 232 and provided so as to move upwards and downwards, and one of the long holes 230 and one of the plungers 232 correspond to the suction and ejection element 231. A connection jig 234 having a cross section in L shape engaging and connected to the protrusion 246 is supported through bearings on the bottom side of the two facing external sides of the block 228 in order to mount the dispenser tip integrated body 226 on the nozzle for attachment integrated body 224 with the suction and ejection mechanism.

FIG. 13(*b*) is a diagram showing the nozzle for attachment integrated body 224 with a suction and ejection mechanism as viewed from the side of the end surface with openings 229. As shown in the Figure, the nozzles for attachment 250 are provided and have an inner diameter that is smaller than the inner diameter of the long holes 230 where the plungers 232 are provided so as to be slidable. The end surface with openings 229 is provided with trenches 248 in grid form, into which the wall plates 245 aligned in grid form can be inserted.

FIG. 14 shows cross sections of the nozzle for attachment integrated body 224 with a suction and ejection mechanism and the dispenser tip integrated body 226 as well as the operation at the time of mounting.

As shown in FIG. 14(*a*), the trenches 248 are filled in with a packing 249 made of a rubber in order to have water tightness and air tightness against the wall plates 245 inserted into the trenches 248. The symbol 252 indicates the end portion of the plunger 232 that slides along the inner wall surface of the long holes 230.

As shown in FIGS. 14(*b*) and 14(*c*), in order to mount the dispenser tip integrated body 226 on the nozzle for attachment integrated body 224 with a suction and ejection mechanism, the upper end of the wall plates 245 aligned in grid form of the dispenser tip integrated body 226 is inserted into the trenches 248 aligned in grid form so that the upper end is made to make contact with the packing 249. Next, the connection jig 234 is rotated around the axis 235 by a quarter of the circumference so that the end portion of the connection jig 234 is engaged with the protrusion 246, and thus, the dispenser tip integrated body 226 is mounted on the nozzle for attachment integrated body 224 with a suction and ejection mechanism.

The embodiments are described in the above for a better understanding of the present invention and do not limit the invention. Accordingly, modifications are possible within such a scope that the gist of the invention is not changed. Nozzles are described only in the case where dispenser tips are mounted on the nozzles, but they are not limited to this example, and nozzles on which no dispenser tips are mounted may be used. In addition, a suction and ejection mechanism is described only in the case where a cylinder is used for this, but it may be used with a mechanism for changing the form of the dispenser tips when bellows type dispenser tips having openings through which sucked and ejected liquid can flow into and flow out of through the expansion and contraction of the inside of a containing portion which can contain a liquid and a gas within wall surfaces as a result of a change in the form of the wall surface connected to the containing portion having the wall surface of which the form can be changed in a predetermined manner without substantially changing the entire surface area of the wall surfaces are used.

In addition, though a case where a process is carried out using only one nozzle head is described in the above, the invention is not limited to this case, and a number of nozzle heads can be used together. Furthermore, though a case where a standard, normal microplate with 96 wells is used is mainly described above, the invention is not limited to the case of such a microplate and can be applied to microplates of various standards. In addition, though a process for extracting nucleic acid is briefly described as an example of a process, the invention is not limited to such a process and can be used for various processes, for example, a process through which mRNA is extracted and refined, and after that cDNA is synthesized through reverse transcription and refined followed by the synthesizing of cRNA labeled with a fluorescent substance. Here, "rows" and "columns" are defined for the purpose of convenience and can be switched if necessary.

INDUSTRIAL APPLICABILITY

The segmented process apparatus for a microplate and the segmented process method for a microplate according to the present invention relate to fields where processes are required on various types of solutions, for example industrial fields, agricultural fields, such as food processing, produce processing and marine product processing, pharmaceutical fields, medical fields relating to sanitation, insurance, immunity, disease and genetics, chemical or biological fields, and other fields. The present invention is effective particularly in the case where a number of processes using a great number of reagents and substances in parallel for a great number of samples are carried out in sequence in a predetermined order.

Figure 1:
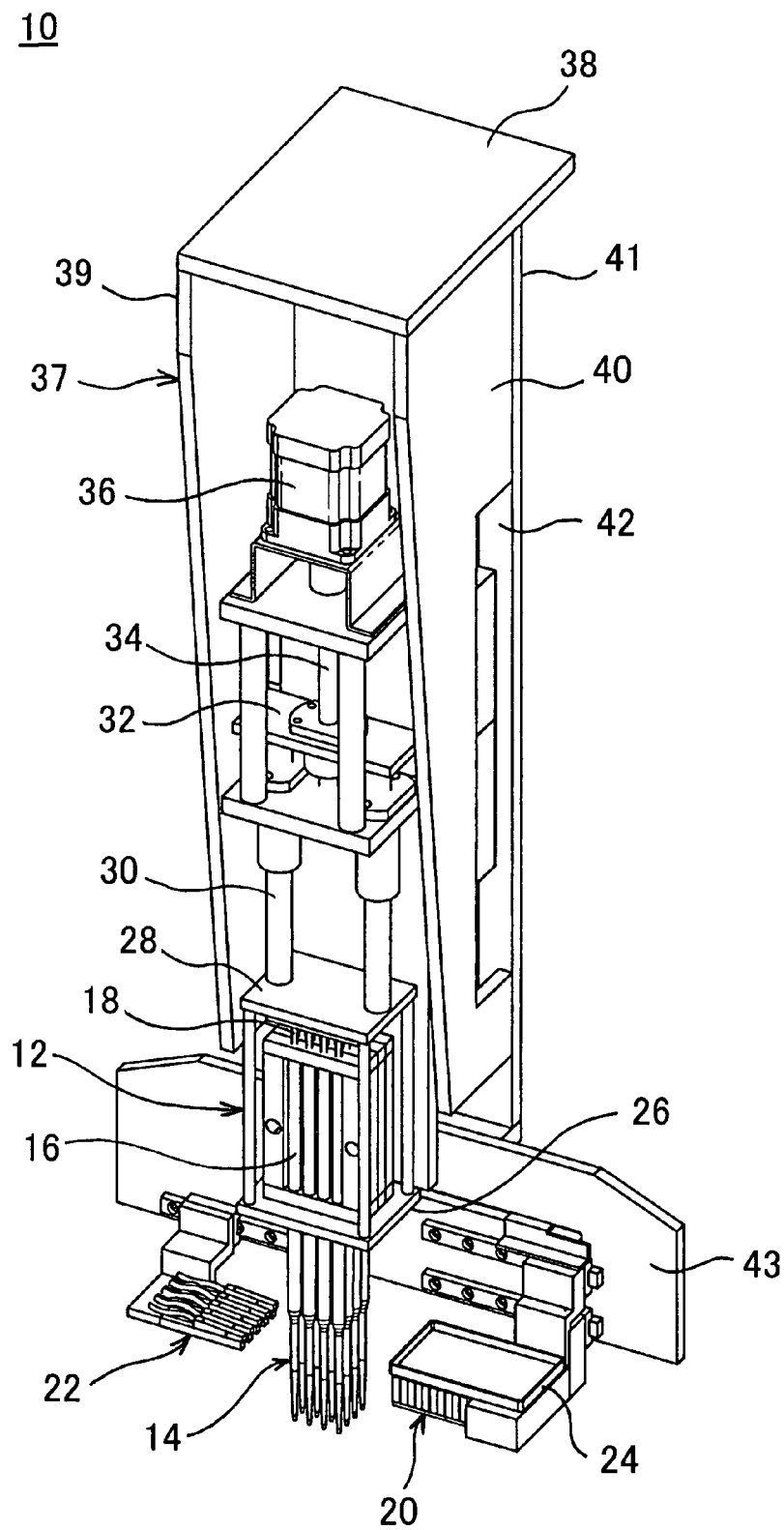
FIG. 1 is a perspective diagram showing the nozzle head of the segmented process apparatus for a microplate according to the first embodiment of the present invention and the periphery thereof.
Figure 2:
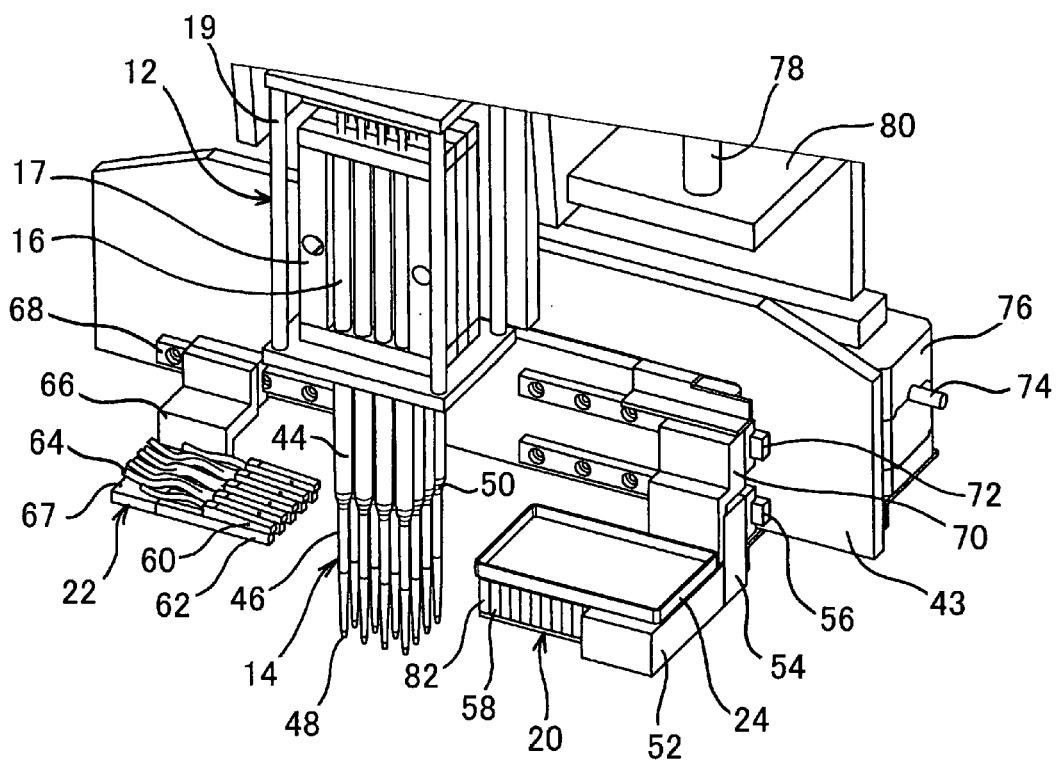
FIG. 2 is a perspective diagram showing an enlargement of a portion of the segmented process apparatus for a microplate shown in FIG. 1.
Figure 3:
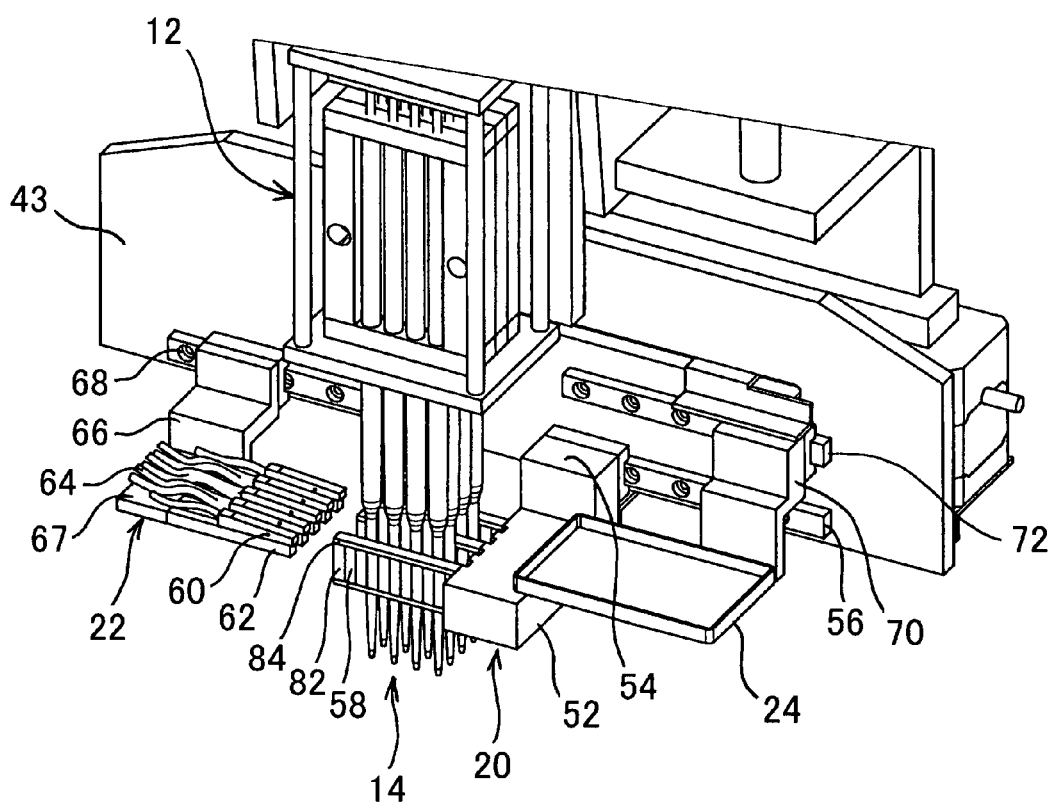
FIG. 3 is a diagram illustrating the operation of the segmented process apparatus for a microplate shown in FIG. 2.
Figure 4:
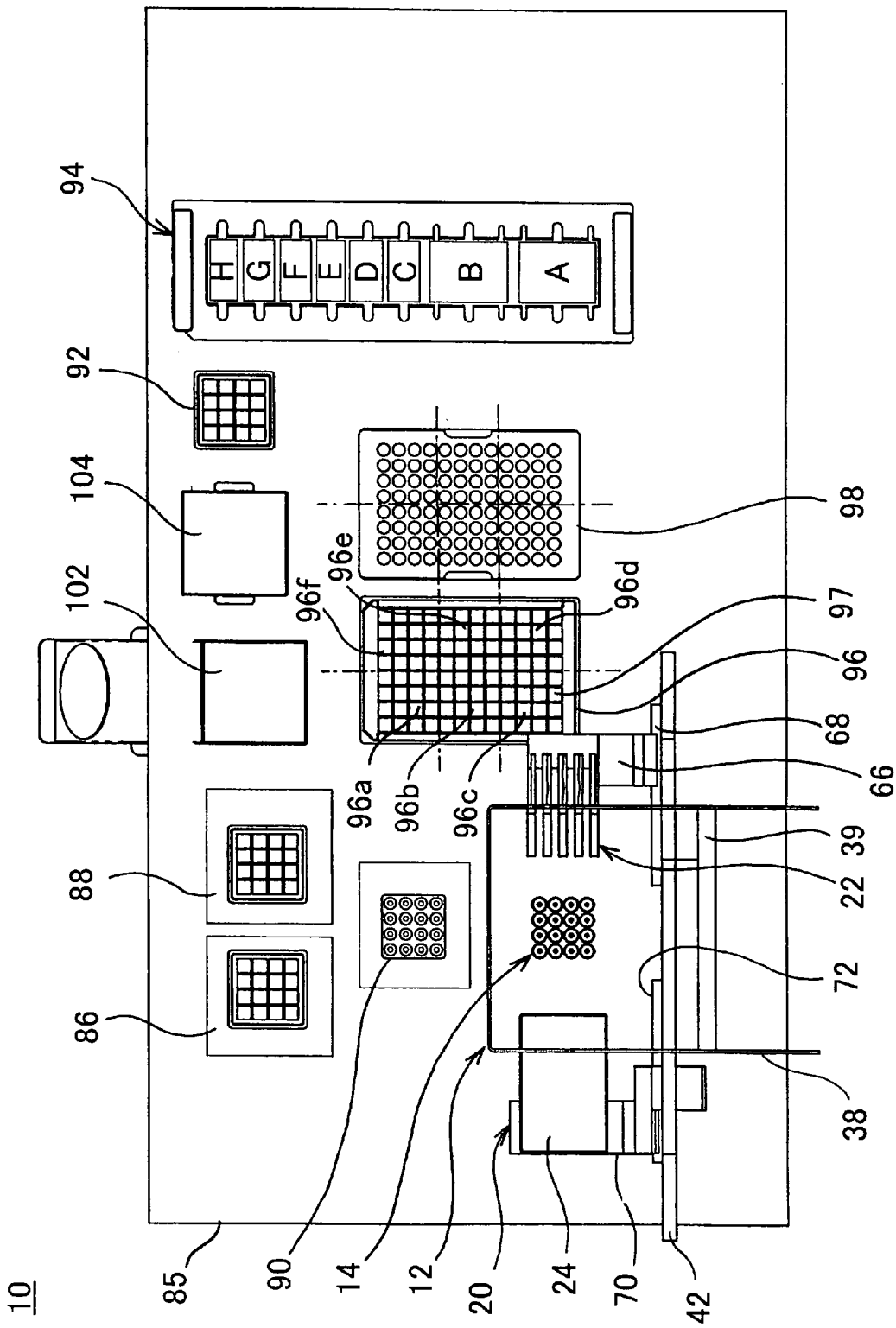
FIG. 4 is a plan diagram showing the entirety of the segmented process apparatus for a microplate according to the first embodiment of the present invention.
Figure 5:
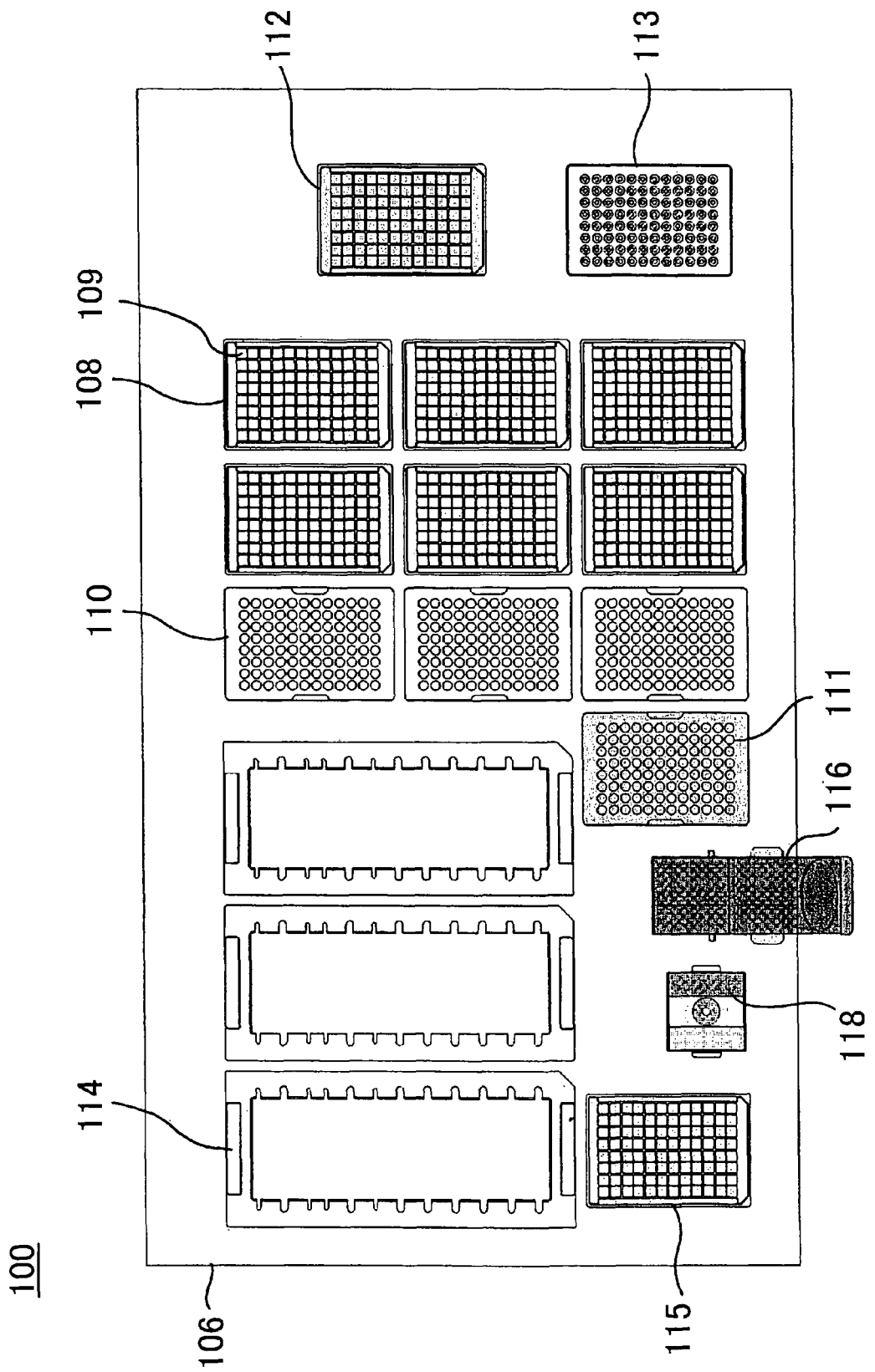
FIG. 5 is a plan diagram showing a group of containers of the segmented process apparatus for a microplate according to the second embodiment of the present invention.
Figure 6:
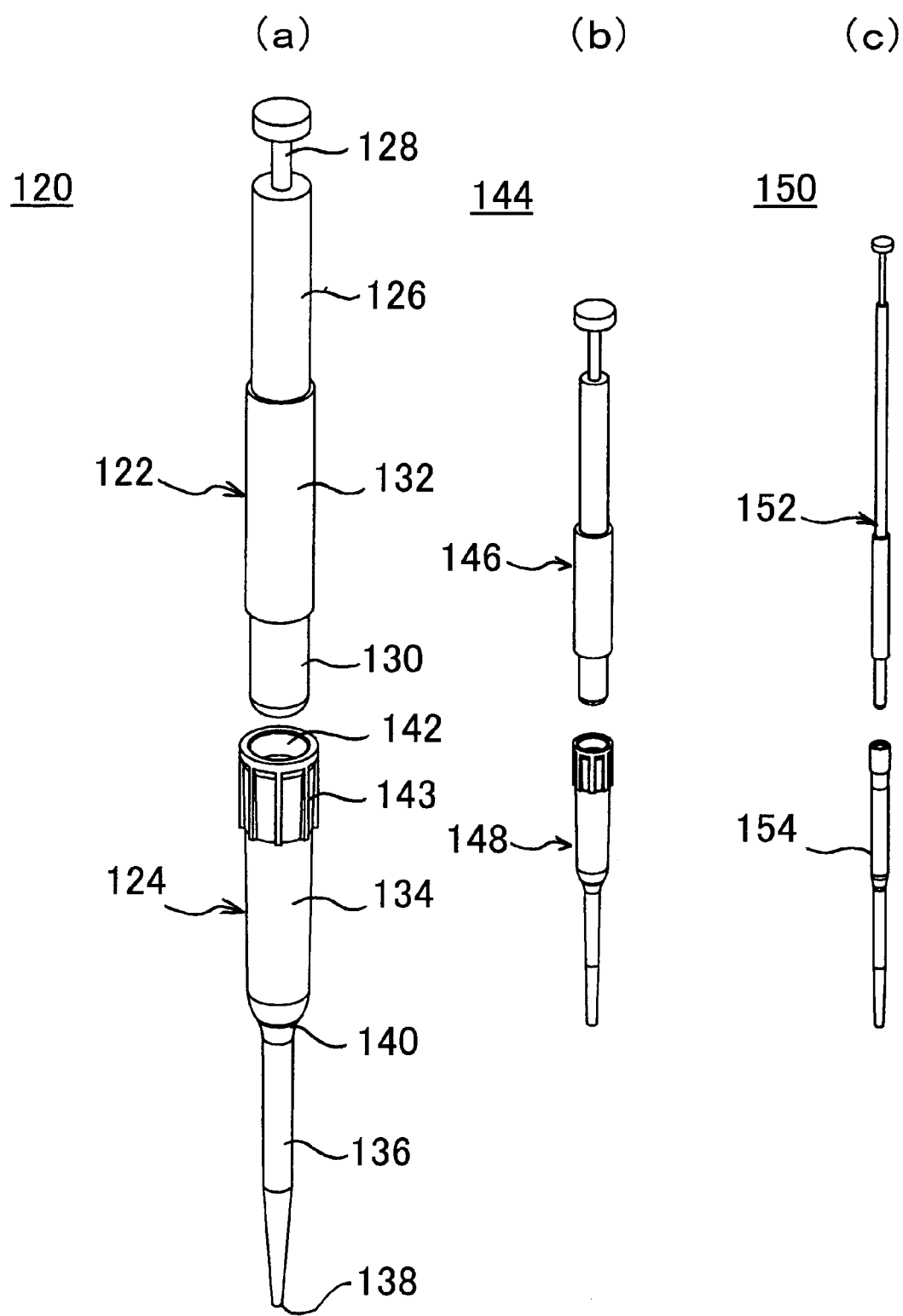
FIG. 6 is a perspective diagram showing nozzles used in the segmented process apparatus for a microplate according to the third, fourth and fifth embodiments of the present invention.
Figure 7:
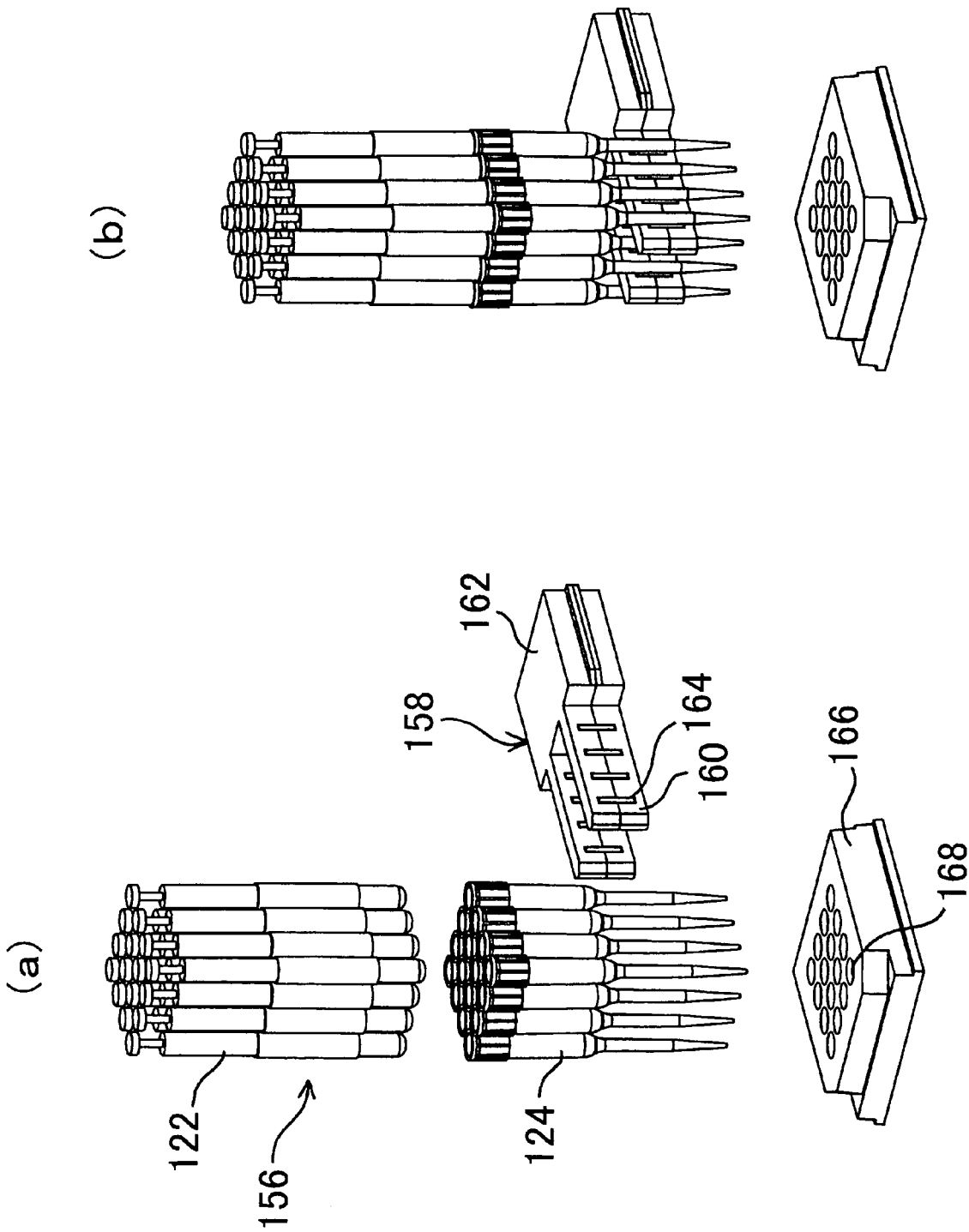
FIG. 7 is a perspective diagram showing the nozzle head portion of the segmented process apparatus for a microplate according to the third embodiment of the present invention.
Figure 8:
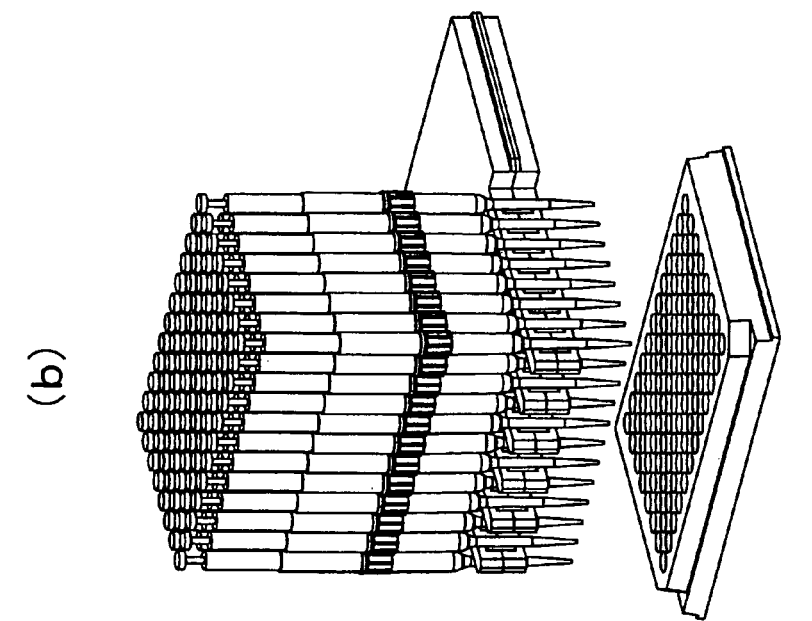
FIG. 8 is a perspective diagram showing the nozzle head portion of the segmented process apparatus for a microplate according to the fourth embodiment of the present invention.
Figure 8:
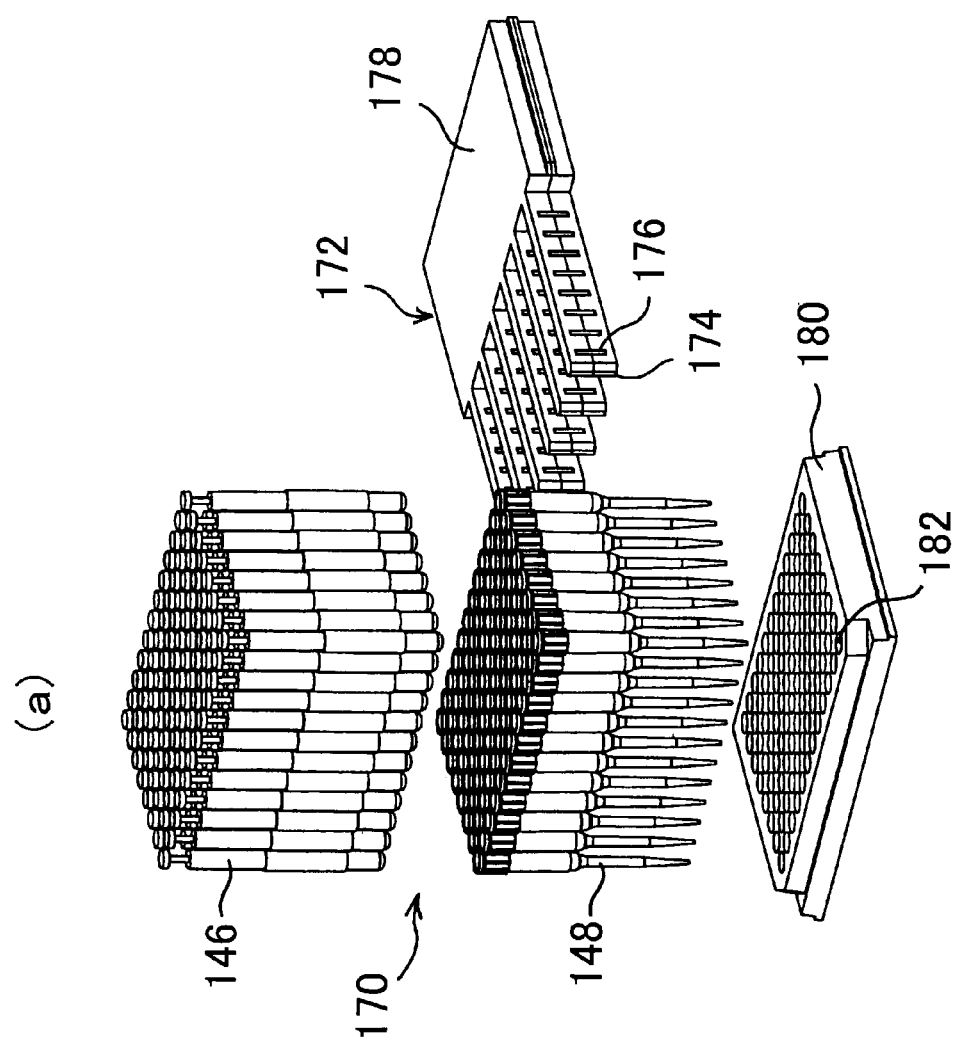
Figure 9:
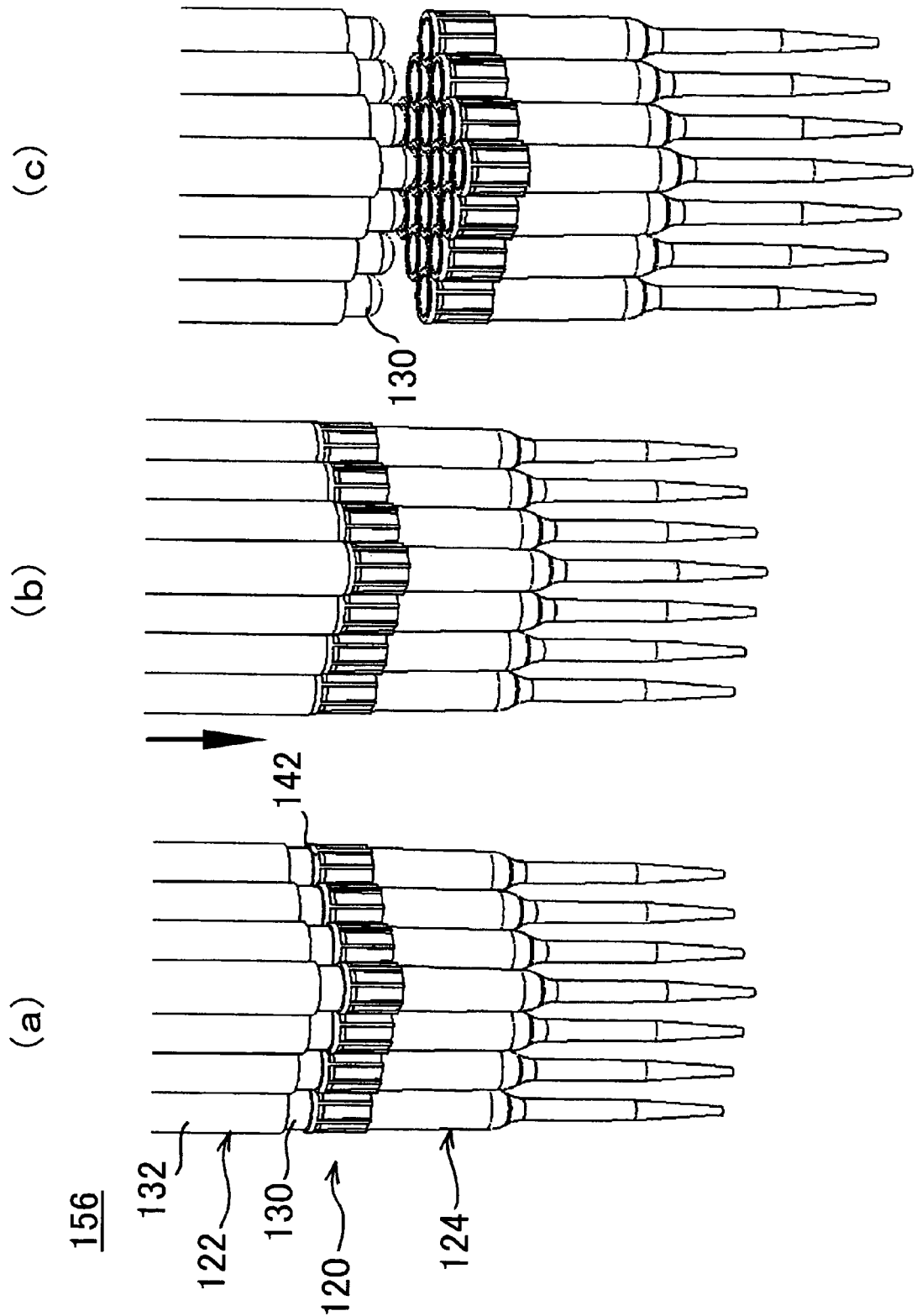
FIG. 9 is a perspective diagram showing the detaching scheme of the segmented process apparatus for a microplate according to the third embodiment of the present invention.
Figure 10:
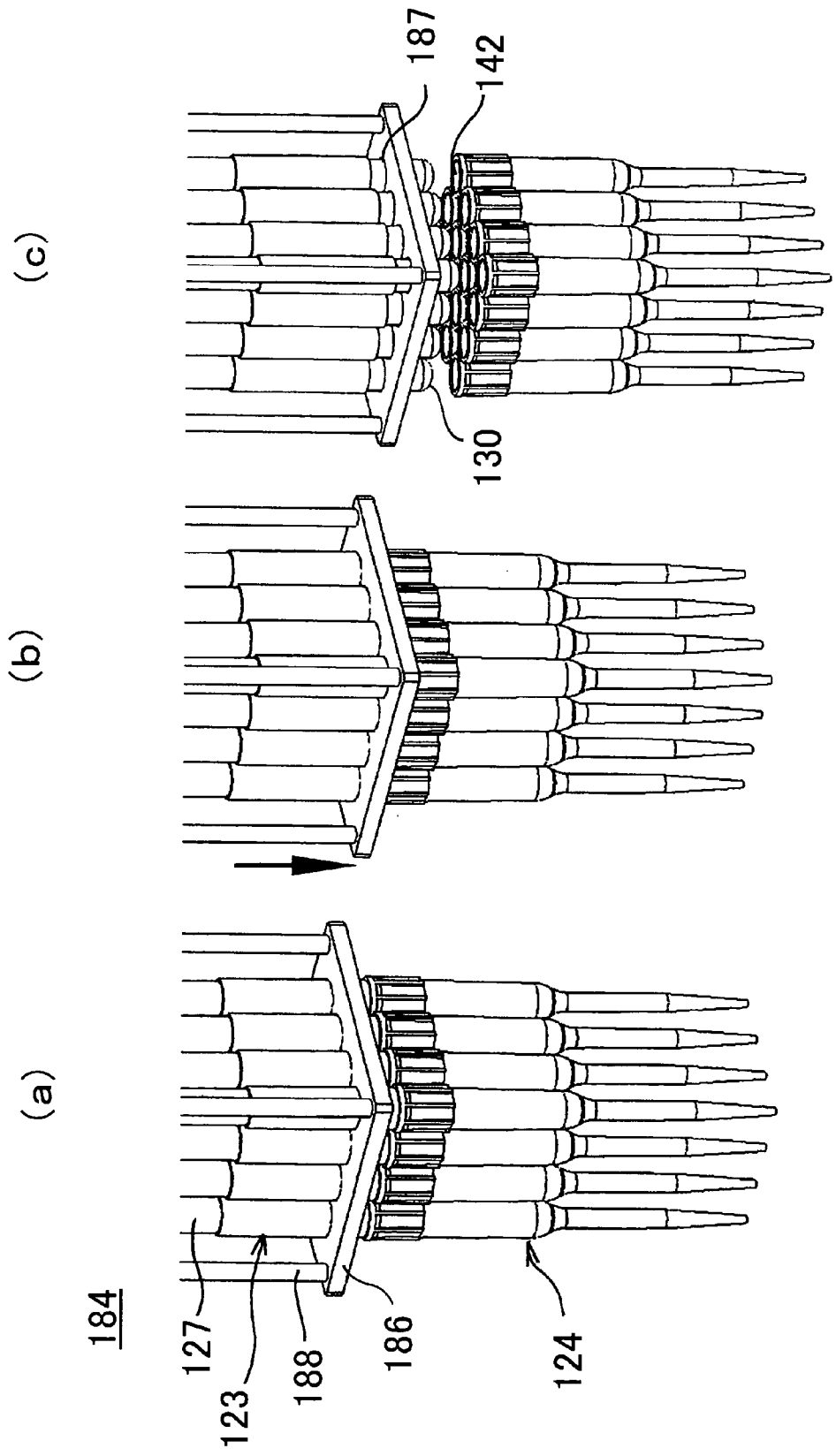
FIG. 10 is a perspective diagram showing the removal scheme of the segmented process apparatus for a microplate according to the sixth embodiment of the present invention.
Figure 11:
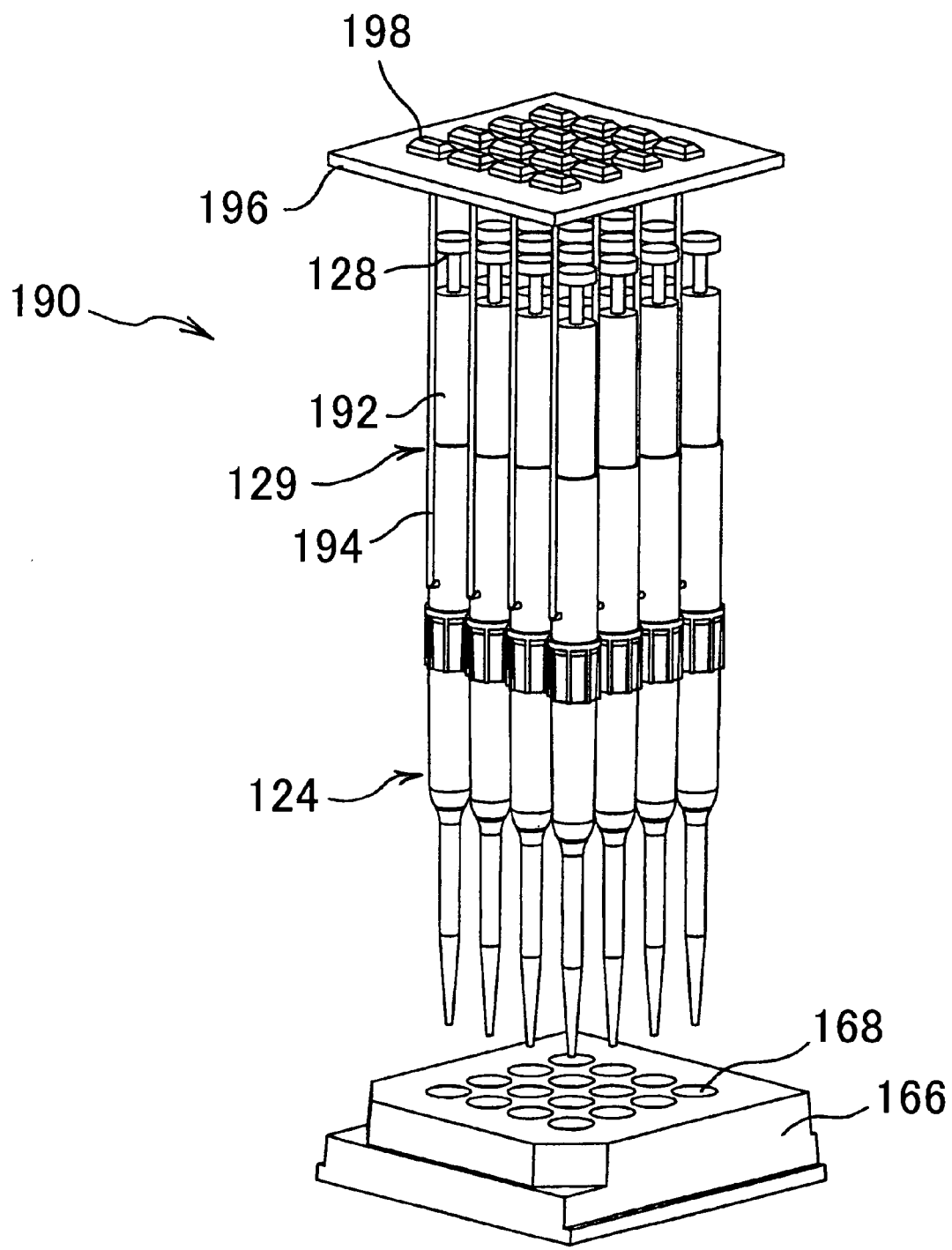
FIG. 11 is a perspective diagram showing the nozzle head portion of the segmented process apparatus for a microplate according to the seventh embodiment of the present invention.
Figure 12:
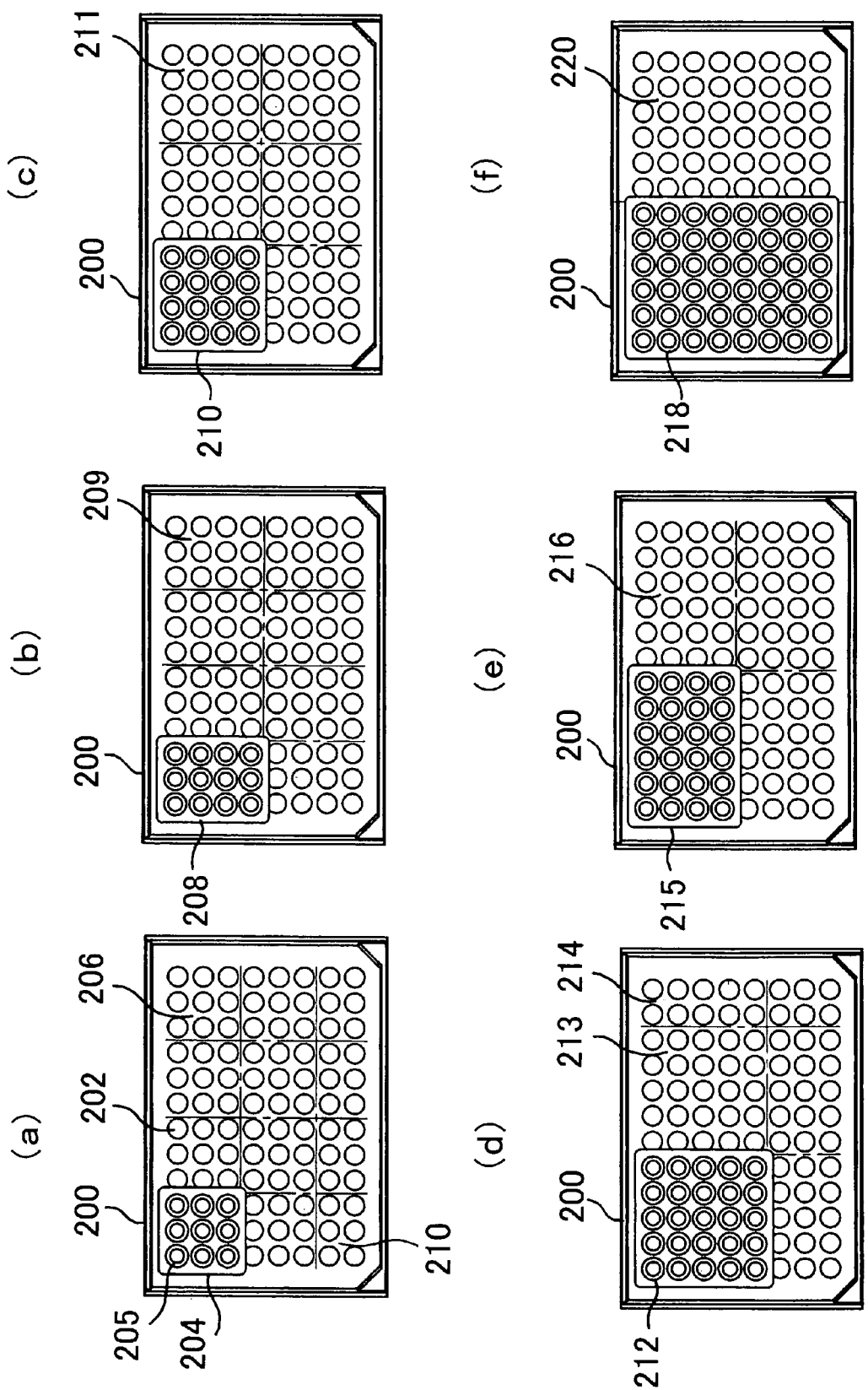
FIG. 12 is a plan diagram showing sub-arrays of wells and nozzle heads of various types of apparatuses for a segmented process for a microplate according to the present invention.
Figure 13:
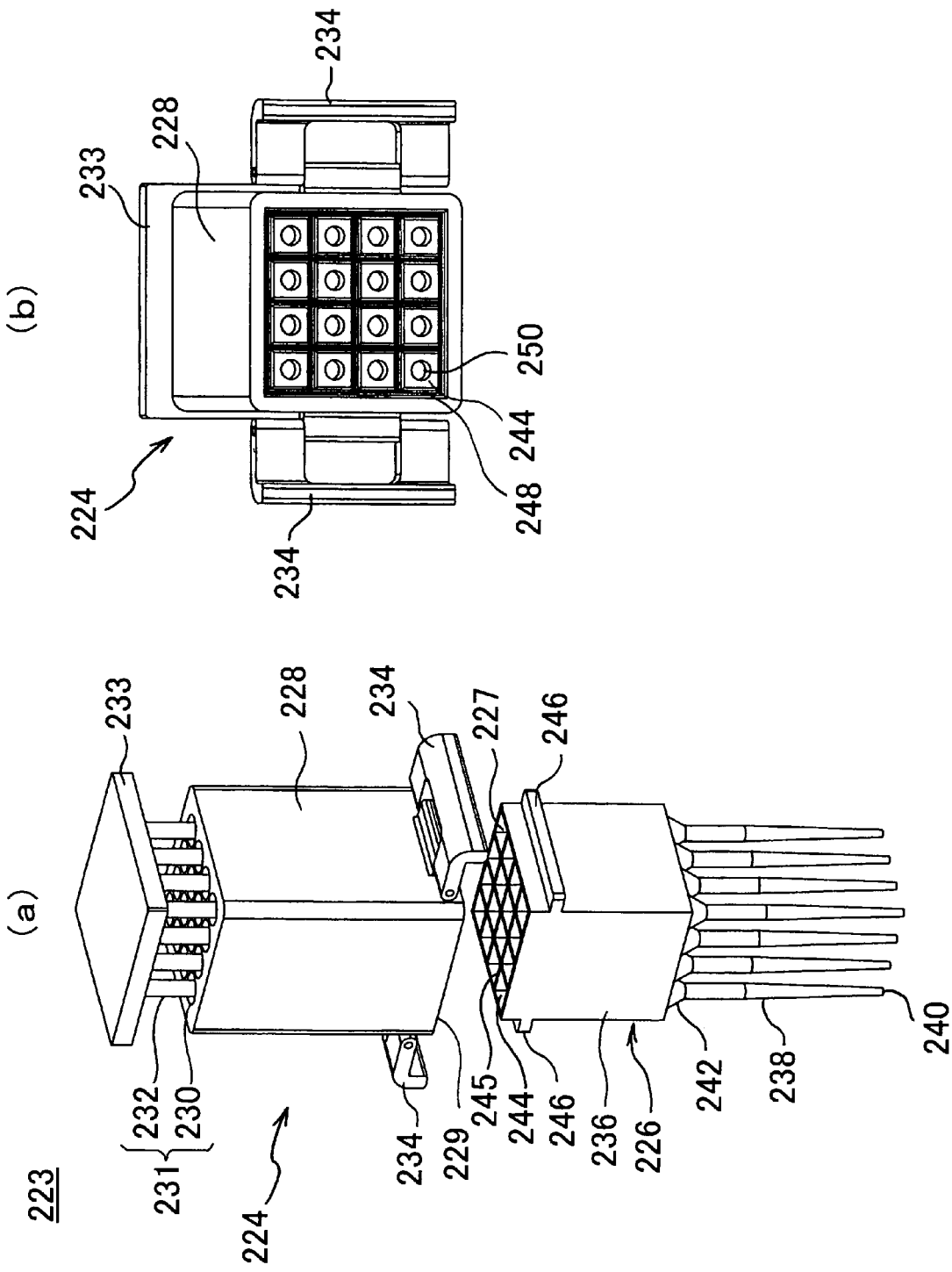
FIG. 13 is a perspective diagram showing the nozzle head of the segmented process apparatus for a microplate according to the eighth embodiment of the present invention.
Figure 14:
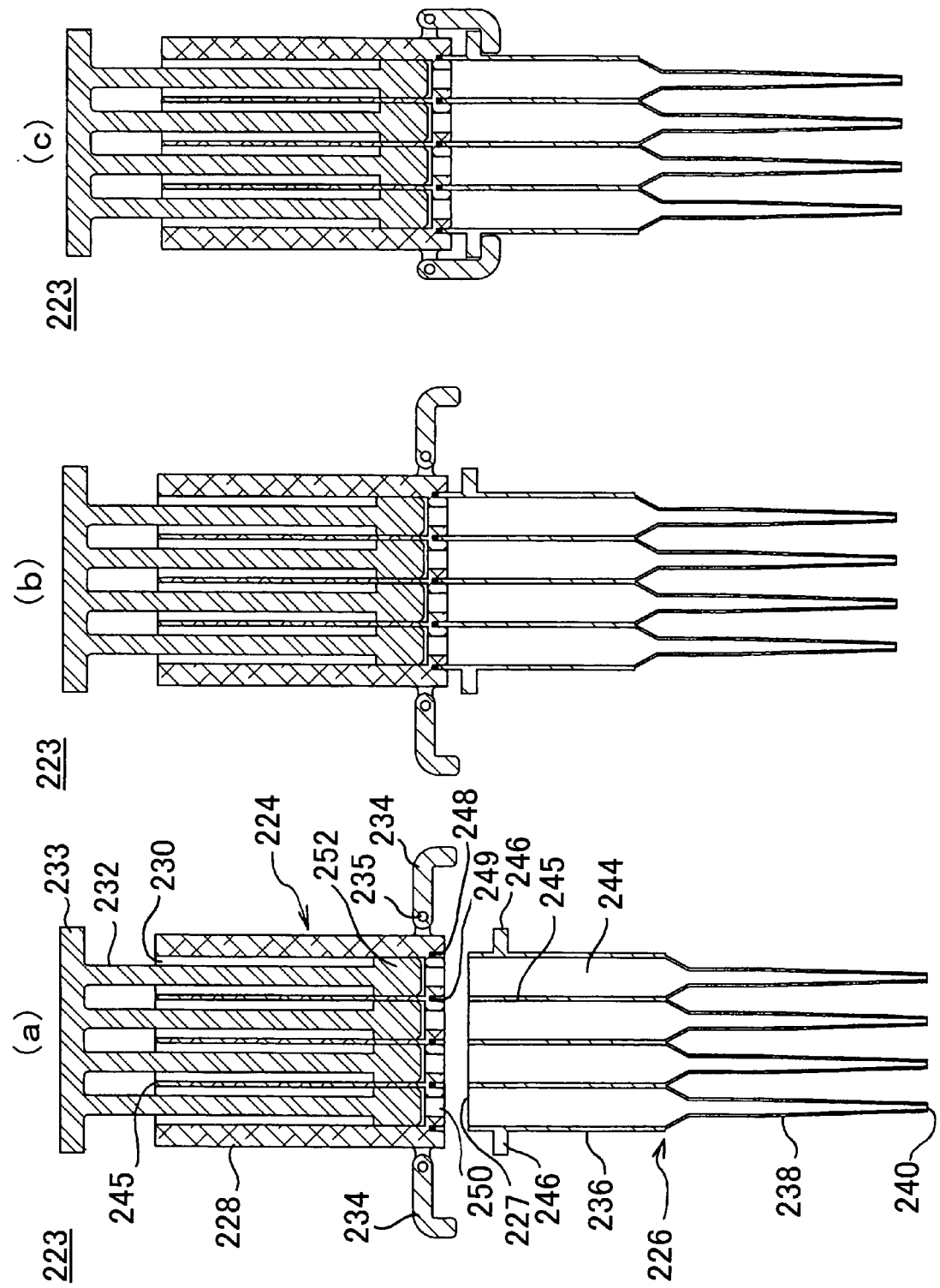
FIG. 14 is a cross sectional diagram showing the nozzle head of the segmented process apparatus for a microplate according to the eighth embodiment of the present invention.

EXPLANATION OF SYMBOLS 10, 100 apparatus for segmented process for microplate
12, 156, 170, 184, 190, 223 nozzle head
14, 124, 148, 154 dispenser tip
16 cylinder
20 magnet in comb teeth form (magnetic force means)
22 light detector in comb teeth form (light detecting means)
96, 108 standard, normal microplate (deep wells)
96a to 96f sub-array of wells
97 deep well
200 standard, normal microplate
120, 144, 150 nozzle
122, 123, 129, 146, 152 nozzle for attachment

The invention claimed is:

1. A segmented process apparatus for a microplate, comprising:
a predetermined microplate provided with a number of wells set in array; one or more nozzle heads provided with a plurality of nozzles set in array, the array of nozzles comprising either two or more nozzle columns where the nozzles are aligned in a column direction, or two or more nozzle rows where the nozzles are aligned in a row direction; a suction and ejection mechanism for sucking and ejecting a gas via the nozzles; and a moving means which allows relative movement between said microplate and the nozzle heads, wherein
tips of all of the nozzles provided on each nozzle head are provided in such a manner that the tips can be inserted into the wells in a part of said microplate all together, and the row intervals and column intervals of said nozzles in array are respectively same as the row intervals and column intervals of said wells in array, and a magnetic force means comprising at least two magnets spaced at the row interval or the column interval of said nozzles;

wherein the magnetic force means is provided in such a manner that the two magnets are movable toward and away from said nozzles along either:

a first straight line that runs either in the column direction or in the row direction so as to run between either two of the nozzle columns or two of the nozzle rows, or a curve that shows a second straight line when projected on a horizontal surface, wherein the curve runs either in the column direction or in the row direction so as to run between either the two of the nozzle columns or the two of the nozzle rows, wherein either the first straight line or the curve passes in the vicinity of each of said nozzles without crossing either of said nozzles, so that it is possible to apply a magnetic field to and remove a magnetic field from inside each of the nozzles provided on said nozzle head all together, wherein the two magnets are movable toward said nozzles along either the first straight line or the curve to insert the two magnets between either the two of the nozzle columns or the two of the nozzle rows, and wherein, after the two magnets have been moved along either the first straight line or the curve and inserted between either the two of the nozzle columns or the two of the nozzle rows, one of the two magnets is positioned between, and adjacent, respective first nozzles in either the two of the nozzle columns or the two of the nozzle rows, and the other of the two magnets is positioned between, and adjacent, respective second nozzles in either the two of the nozzle columns or the two of the nozzle rows.

2. The segmented process apparatus for a microplate according to claim 1, wherein said microplate includes a number of sub-arrays of wells into each of which the tips of all of the nozzles provided on said nozzle head can be inserted all together, and each of the sub-arrays does not include a well overlapping with each other.

3. The segmented process apparatus for a microplate according to claim 2, further comprising a control portion, wherein the control portion controls said moving means to perform an operation, in which the moving means relatively moves between said nozzle head and said microplate so that the tips of all of the nozzles provided on said nozzle head are in such locations where the tips can be inserted into the wells belonging to one of said sub-arrays of wells in said microplate, and then moves to insert the tips of said nozzles into said wells all together and to remove the tips after a certain process, and the operation is repeated in sequence for the wells belonging to other sub-arrays of wells.

4. The segmented process apparatus for a microplate according to claim 3, wherein solutions or suspension liquids required for the steps in the process are contained in each of said number of sub-arrays of wells along the moving path of said nozzle head in accordance with the order of the steps.

5. The segmented process apparatus for a microplate according to claim 1, wherein said magnetic force means includes: one or more comb teeth members in rod form, which extend in the row direction or the column direction and which are correspondingly aligned in the column direction or the row direction so as to come adjacent to one or two nozzle rows or nozzle columns, at least one of the comb teeth members having a width sized to permit it to be inserted between either the two of the nozzle columns or the two of the nozzle rows; a support member connected one or more of the comb teeth members at one end and is movable relative to said nozzles; and a plurality of magnets provided in each comb teeth member in locations corresponding to the nozzles belonging to said one or two nozzle rows or nozzle columns adjacent to each other; wherein said two magnets are part of the plurality of magnets provided in the at least one of the comb teeth members.

6. The segmented process apparatus for a microplate according to claim 1, wherein each of said nozzles provided on said nozzle head has an attachment nozzle and a dispenser tip detachably attached to said attachment nozzle, and said nozzle head has a tip detaching portion for detaching the dispenser tip attached to said attachment nozzle.

7. The segmented process apparatus for a microplate according to claim 1, further comprising a light detecting means having a light detecting portion provided in such a manner that the light detecting unit is movable toward each of the nozzles in sequence along a third straight line or a second curve that passes in the vicinity of each of said nozzles without crossing either of said nozzles so that it is possible to detect the state of the liquid inside the nozzles provided on said nozzle head in sequence, wherein the third straight line runs either in the column direction or in the row direction so as to run between either the two of the nozzle columns or the two of the nozzle rows, and wherein the second curve runs either in the column direction or in the row direction so as to run between either the two of the nozzle columns or the two of the nozzle rows.

8. The segmented process apparatus for a microplate according to claim 7, wherein said light detecting means includes: one or more comb teeth members in rod form, which extend in the row direction or the column direction and which are correspondingly aligned in the column direction or the row direction so as to come adjacent to one or two nozzle rows or nozzle columns; a support member connected to the one or more comb teeth members at one end and movable relative to said nozzles; and light detecting portions provided in the vicinity of the other end of said comb teeth members in order to optically detect the inside of the nozzles belonging to one or two nozzle rows or nozzle columns adjacent to each other in sequence.

9. The segmented process apparatus for a microplate according to claim 1, wherein said nozzle head has an integrated nozzle body where two or more nozzles set in array are integrated, and said suction and ejection mechanism has two or more suction and ejection elements connected to the two or more nozzles of said integrated nozzle body, wherein the two or more nozzles are integrated in such a manner that portions for storing a liquid are separated with only one wall plate.

* * * * *